US009623239B2

(12) United States Patent
Francois et al.

(10) Patent No.: US 9,623,239 B2
(45) Date of Patent: *Apr. 18, 2017

(54) APPARATUS AND METHODS FOR ASSISTING BREATHING

(71) Applicant: Apellis Holdings, LLC, Crestwood, KY (US)

(72) Inventors: Cedric Francois, Crestwood, KY (US); Angus McLachlan, Crestwood, KY (US)

(73) Assignee: Apellis Holdings, LLC, Crestwood, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/858,246

(22) Filed: Sep. 18, 2015

(65) Prior Publication Data

US 2016/0067484 A1    Mar. 10, 2016

Related U.S. Application Data

(63) Continuation of application No. 13/981,657, filed as application No. PCT/US2012/022547 on Jan. 25, 2012, now Pat. No. 9,174,046.

(Continued)

(51) Int. Cl.
*A61N 1/00* (2006.01)
*A61N 1/36* (2006.01)
(Continued)

(52) U.S. Cl.
CPC .......... *A61N 1/3601* (2013.01); *A61B 5/0806* (2013.01); *A61B 5/6804* (2013.01); *A61H 31/00* (2013.01); *A61N 1/36014* (2013.01);

*A61B 5/1135* (2013.01); *A61B 5/7264* (2013.01); *A61H 9/0078* (2013.01); *A61H 2011/005* (2013.01); *A61H 2201/10* (2013.01); *A61H 2201/165* (2013.01);
(Continued)

(58) Field of Classification Search
CPC .......................... A61N 1/3601; A61N 1/36003
USPC ...................................... 607/42, 48
See application file for complete search history.

(56) References Cited

U.S. PATENT DOCUMENTS 4,004,579 A    1/1977  Dedo
4,763,660 A    8/1988  Kroll et al.
(Continued)

FOREIGN PATENT DOCUMENTS

WO    0041764    7/2000
WO    0103581    1/2001
(Continued)

OTHER PUBLICATIONS

Abstract of Golee et al, "A control system for automatic electrical stimulation of abdominal muscles to assist respiratory function in tetraplegia":; Med Eng Phys. Dec. 2007; 1180-1.
(Continued)

*Primary Examiner* — Nadia A Mahmood
(74) *Attorney, Agent, or Firm* — Dinsmore & Shohl LLP

(57) ABSTRACT

The present invention provides, among other things, apparatus and methods of use for treating a subject in need of assistance with breathing. In some embodiments the subject suffers from airflow obstruction. In some embodiments, the subject suffers from chronic obstructive pulmonary disease.

20 Claims, 3 Drawing Sheets

Related U.S. Application Data

(60) Provisional application No. 61/436,010, filed on Jan. 25, 2011.

(51) Int. Cl.

| | | |
|---|---|---|
| *A61H 31/00* | (2006.01) | |
| *A61B 5/08* | (2006.01) | |
| *A61B 5/113* | (2006.01) | |
| *A61B 5/00* | (2006.01) | |
| *A61H 9/00* | (2006.01) | |
| *A61H 11/00* | (2006.01) | |

(52) U.S. Cl.
CPC ............... *A61H 2201/1619* (2013.01); *A61H 2201/5007* (2013.01); *A61H 2201/5015* (2013.01); *A61H 2201/5035* (2013.01); *A61H 2201/5046* (2013.01); *A61H 2201/5061* (2013.01); *A61H 2201/5082* (2013.01); *A61H 2201/5084* (2013.01); *A61H 2205/083* (2013.01); *A61H 2230/065* (2013.01); *A61H 2230/208* (2013.01); *A61H 2230/305* (2013.01); *A61H 2230/405* (2013.01); *A61H 2230/505* (2013.01); *A61H 2230/605* (2013.01); *A61H 2230/625* (2013.01)

(56) References Cited

U.S. PATENT DOCUMENTS

| | | | |
|---|---|---|---|
| 4,838,263 | A | 6/1989 | Warwick et al. |
| 4,977,889 | A | 12/1990 | Budd |
| 5,131,399 | A | 7/1992 | Sciarra |
| 5,913,830 | A | 6/1999 | Miles |
| 6,030,353 | A | 2/2000 | Van Brunt |
| 6,249,076 | B1 | 6/2001 | Madden et al. |
| 6,341,237 | B1 | 1/2002 | Hurtado |
| 6,360,740 | B1 | 3/2002 | Ward et al. |
| 6,376,971 | B1 | 4/2002 | Pelrine et al. |
| 6,383,143 | B1 | 5/2002 | Rost |
| 6,545,384 | B1 | 4/2003 | Pelrine et al. |
| 7,491,185 | B2 | 2/2009 | Couvillon, Jr. |
| 2002/0010495 | A1 | 1/2002 | Freed |
| 2002/0077688 | A1 | 6/2002 | Kirkland |
| 2002/0103513 | A1 | 8/2002 | Minogue et al. |
| 2003/0028131 | A1 | 2/2003 | Van Brunt et al. |
| 2004/0039426 | A1 | 2/2004 | Hurtado |
| 2005/0165334 | A1 | 7/2005 | Lurie |
| 2006/0247729 | A1* | 11/2006 | Tehrani ............... A61N 1/3601 607/42 |
| 2008/0077192 | A1 | 3/2008 | Harry et al. |
| 2008/0109047 | A1* | 5/2008 | Pless ................... A61N 1/3601 607/42 |
| 2008/0167586 | A1 | 7/2008 | Baldauf et al. |
| 2008/0275356 | A1 | 11/2008 | Stasz et al. |
| 2009/0093740 | A1 | 4/2009 | Helgeson et al. |
| 2009/0234256 | A1 | 9/2009 | Helgeson et al. |
| 2009/0259135 | A1 | 10/2009 | Stasz |
| 2009/0299430 | A1 | 12/2009 | Davies et al. |
| 2010/0004715 | A1 | 1/2010 | Fahey |
| 2010/0076518 | A1 | 3/2010 | Hlavka et al. |
| 2010/0087748 | A1 | 4/2010 | Tobola et al. |
| 2010/0095965 | A1 | 4/2010 | Piper |
| 2010/0185253 | A1 | 7/2010 | DiMarco et al. |
| 2010/0286546 | A1 | 11/2010 | Tobola et al. |
| 2010/0298905 | A1 | 11/2010 | Simon |

FOREIGN PATENT DOCUMENTS

| | | |
|---|---|---|
| WO | 2006003429 | 1/2006 |
| WO | 2006113802 | 10/2006 |
| WO | 2006121463 | 11/2006 |
| WO | 2006127573 | 11/2006 |
| WO | 2007112527 | 10/2007 |
| WO | 2008136980 | 11/2008 |
| WO | 2010071919 | 7/2010 |
| WO | 2010136486 | 12/2010 |

OTHER PUBLICATIONS

Abstract of Stanic U et al, "Funcitonal Electrical Stimulation of Abdominal Muscles to Augment Tidal Volume in Spinal Cord Injury"; IEEE Tran Rehabil Eng. Mar. 2000; 8(1); 30-4.

Abstract of Sorli J. et al, "Ventilatory Assistance Using Electrical Stimulation of Abdominal Muscles"; IEEE Trans Rehabil Eng. Mar. 1996; 4(1): 1-6.

Gollee, H. et al, "Abdominal Stimulation for Respiratory Support in Tetraplegia: a Tutorial Review"; Journal of Automatic control, University of Belgrade, vol. 18(2): 85-92, 2008.

Hopkinson, Nicholas et al, "Abdominal Muscle Fatigue Following Exercise in Chronic Obstructive Pulmonary Disease"; Respiratory Research, 2010, 11:15.

Giorgino, T. et al, "Assessment of Sensorized Garments as a Flexible Support to Self-Administered Post-Stroke Physical Rehabilitation"; Eur J Phys Rehabil Med 2009: 45:75-84.

Porcari, John et al, "The Effects of Neuromuscular Electrical Stimulation Training on Abdominal Strength, Endurance, and Selected Anthropometric Measures"; Journal of Sports Science and Medicine (2005) 4, 66-75.

O'Donnell, D. E. et al, "Physiology and Cponsequences of Lung Hyperinflation in COPD"; Eur Respir Rev 2006 15:100. 61-67.

Lim, Julianne et al, "Optimal Electrode Placement for Non-Invasive Electrical Stimulation of Human Abdominal Muscles"; J Appl Physiol 102: 1612-1617, 2007.

Clarenbach, Christian et al, "Monitoring of Ventilation During Exercise bya Portable Respiratory Inductive Plethysmograph"; Chest 2005; 128; 1282-1290.

Bach, John R., "Mechanical Exsufflation, Noninvasive Ventilation, and New Strategies for Pulmonary Rehabilitation and Sleep Disordered Breathing"; New Jersey Medical School, vol. 68, No. 2, Mar.-Apr. 1992.

Dimarco, Anthony et al, "Lower Thoracic Spinal Cord Stimulation to Restore Cough in Patients with Spinal Cord Injury: Results of a National Institute of Health-Sponsored Clinical Trial Part I: Methodology and Effectiveness of Expiratory Muscle Activation"; Arch Phys Med Rehabil. May 2009; 90(5): 717.

Bach, J.R. et al, "Intermittent Abdominal Pressure Ventilator in a Regimen of Noninvasive Ventilatory Support"; Chest 1991; 99; 630-636.

Kandare, Franc et al, "Breathing Induced by Abdominal Muscle Stimulations in Individuals Without Spontaneous Ventilation"; 2002 International Neuromodulation Society, vol. 5, No. 3, 180-185.

Letter to the Editor for Gollee 2007; Medical Engineering & Physics 29 (2007) 1180-1181.

* cited by examiner

APPARATUS AND METHODS FOR ASSISTING BREATHING

CROSS-REFERENCE TO RELATED APPLICATION

This application is a continuation of U.S. application Ser. No. 13/981,657 filed on Feb. 6, 2014, which is a §371 of International Application No. PCT/US2012/022547 filed on Jan. 25, 2012, and which claims the benefit of U.S. Provisional Application Ser. No. 61/436,010, filed on Jan. 25, 2011, the entire disclosures of which are incorporated herein by this reference.

BACKGROUND OF THE INVENTION

Disorders affecting the respiratory system are significant causes of morbidity and mortality. Chronic obstructive lung disease (COPD) is a common disease whose prevalence is expected to rise considerably over the next two decades. COPD can have debilitating effects on a patient's daily functioning and quality of life. Pharmacological therapies such as bronchodilators and corticosteroids are widely used in the treatment of COPD. A variety of non-pharmacological treatment modalities are also available. However, a significant proportion of patients experience persistent symptoms despite such interventions. There is a need for innovative approaches to help manage COPD.

SUMMARY OF THE INVENTION

The invention provides, in some aspects, a method of treating a subject comprising: (a) sensing when a subject is exhaling; and (b) delivering a stimulus to the subject's thorax or abdomen during at least part of the expiratory phase of breathing in response to said sensing, so as to assist the subject with exhalation. In some embodiments the subject suffers from chronic obstructive pulmonary disease (COPD). In some embodiments the subject suffers from hyperinflation of the lungs. In some embodiments performing the method decreases the subject's end expiratory lung volume (EELV) as compared with the subject's EELV when unassisted. In some embodiments the subject has an abnormally high EELV in the absence of the stimulus. In some embodiments the subject suffers from dynamic hyperinflation in the absence of the stimulus. In some embodiments, step (a) comprises detecting respiratory movement of the subject's thorax or abdomen. In some embodiments, step (a) comprises detecting respiratory movement of the subject's thorax or abdomen using inductive plethysmography. In some embodiments, step (a) comprises detecting respiratory movement of the subject's thorax or abdomen using a strain gauge. In some embodiments the sensing is performed at least in part using a sensor that is incorporated into an adhesive patch suitable for placement on the subject's skin. In some embodiments the sensing occurs externally to the subject. In some embodiments the stimulus is delivered externally to the subject. In some embodiments the sensing occurs externally to the subject and the stimulus is delivered externally to the subject. In some embodiments the sensor, device, or both are incorporated into a garment or belt. In some embodiments the sensor and the device are incorporated into the same garment or belt. In some embodiments step (b) comprises delivering electrical stimulation to one or more muscles of expiration and/or to efferent nerve(s) supplying one or more muscles of expiration, wherein said stimulus is sufficient to cause contraction of said muscle(s) or increase the expiratory force generated by said muscle(s). In some embodiments step (b) comprises delivering electrical stimulation to one or more abdominal muscles. In some embodiments step (b) comprises delivering electrical stimulation to the rectus abdominis muscle. In some embodiments step (b) comprises delivering electrical stimulation to one or more lower internal intercostal muscles of the anterior thorax. In some embodiments step (b) comprises mechanically compressing the subject's abdomen or lower anterior thorax. In some embodiments step (b) comprises mechanically compressing the subject's abdomen or lower anterior thorax using a device comprising an inflatable compartment. In some embodiments the stimulus is not delivered while the subject is inhaling. In some embodiments a method comprises determining that the subject has at least one sign or symptom indicative of an abnormally high EELV. In some embodiments a method comprises determining that the subject suffers from COPD. In some embodiments the stimulus is delivered near the onset of exhalation, e.g., within 0.01 seconds and 0.25 seconds of the onset of exhalation. In some embodiments a stimulus is delivered during some but not all respiratory cycles within a session. In some embodiments a method comprises analyzing a subject's breathing pattern or activity level and adjusting one or more stimulus parameters based at least in part on the analysis. In some embodiments a subject is intubated or has recently been extubated.

In another aspect, the invention provides an apparatus comprising: (a) a sensor suitable for detecting when a subject is exhaling; and (b) a device adapted to deliver a stimulus to the subject's thorax or abdomen during at least part of the expiratory phase of the subject's breathing in response to a signal generated by said sensor. In accordance with certain embodiments of the invention, the stimulus is effective to assist the subject with exhalation. In some embodiments the stimulus is an electrical stimulus that stimulates one or more muscle(s) of expiration. In some embodiments, the device stimulates at least some abdominal muscles, e.g., the rectus abdominis muscle. In some embodiments, transcutaneous electrical stimulation is used. In some embodiments the stimulus is effective to assist the subject with exhalation. In some embodiments the stimulus is effective to result in a decrease in the subject's EELV as compared with the subject's EELV without the stimulus. In some embodiments the sensor comprises a strain gauge. In some embodiments the sensor comprises a respiratory inductive plethysmography sensor or piezoelectric sensor. In some embodiments the sensor is incorporated into an adhesive patch suitable for placement on the subject's skin. In some embodiments the sensor is physically connected to the device. In some embodiments the sensor is in wireless communication with the device. In some embodiments the device comprises means for delivering an electrical stimulus to one or more of the subject's muscle(s) of expiration. In some embodiments the device comprises an abdominal muscle stimulator. In some embodiments the apparatus comprises a respiratory inductive plethysmography sensor or piezoelectric sensor and an abdominal muscle stimulator. In some embodiments the device comprises means for mechanically compressing the lower anterior thorax or abdomen. In some embodiments the sensor, the device, or both, are integrated into a garment or belt. In some embodiments the sensor and the device are integrated into the same garment or belt. In some embodiments the device comprises an inflatable compartment that mechanically compresses the subject's lower anterior thorax or abdomen when inflated. In some embodiments the apparatus comprises a power supply.

In some embodiments the power supply is attached to the device. In some embodiments the apparatus comprises a control unit that allows a subject to turn the device on or off. In some embodiments a control unit allows the apparatus to be set at any of two or more modes. In some embodiments a control unit allows selection of a stimulus protocol, one or more stimulus parameters, posture, and/or physical activity. In some embodiments the apparatus comprises a sensor, a signal conditioning unit, a controller, and a stimulator. In some embodiments the apparatus comprises a controller that analyzes a subject's breathing pattern or activity level and adjusts one or more stimulus parameters based at least in part on the analysis. In some embodiments a method of treating a subject comprises providing the subject with an apparatus of the present disclosure. In some aspects, a method of making an apparatus comprises: (a) providing a sensor suitable for sensing when a subject is exhaling; (b) providing a device adapted to deliver a stimulus to a subject's thorax or abdomen wherein said stimulus is effective to assist a subject with exhalation; and (c) linking the sensor and the device so that the sensor can communicate with the device and cause it to deliver the stimulus during at least part of the expiratory phase of the subject's breathing. In some embodiments the apparatus comprises any of the components or features described herein.

In some aspects, a method comprises: delivering an electrical stimulus to one or more of a subject's muscle(s) of expiration or to efferent nerve(s) supplying said muscle(s), so as to cause increased contraction of at least some of said muscle(s) selectively during the expiratory phase of the subject's breathing. In some embodiments the method comprises: (a) sensing when a subject is exhaling; and (b) delivering said stimulus so as to cause increased contraction of at least some of said muscle(s) during at least part of the expiratory phase of the subject's breathing. In some embodiments the stimulus is not delivered while the subject is inhaling.

In some aspects, an apparatus comprises: (a) a sensor suitable for detecting when a subject is exhaling; and (b) a device adapted to deliver an electrical stimulus to at least some of the subject's muscles of expiration during at least part of the expiratory phase of the subject's breathing in response to a signal generated by said sensor, wherein the stimulus is effective to cause or increase contraction of said muscle(s) during at least part of the expiratory phase of the subject's breathing. In some embodiments the sensor comprises a respiratory inductive plethysmography sensor and the device is adapted to deliver a stimulus to at least some of the subject's abdominal muscles. In some embodiments the sensor, device, or both, are integrated into a garment or belt. In some embodiments the sensor comprises a piezoelectric sensor and the device is adapted to deliver a stimulus to at least some of the subject's abdominal muscles. In some embodiments the sensor stimulates at least the rectus abdominis. In some embodiments the apparatus is capable of operating in two or more modes, wherein at least one mode comprises delivering, in response to signals generated by said sensor, tactile stimuli that are sufficient to be felt by the subject but are not effective to affect expiratory muscle contraction. In some embodiments timing of the tactile stimuli is selected so as to prompt the subject to exhale at least a specified volume or for at least a specified time.

In some aspects, an apparatus comprises: (a) a sensor suitable for detecting when a subject is exhaling; and (b) a device adapted to deliver an electrical stimulus to at least some of the subject's muscles of expiration during at least part of the expiratory phase of the subject's breathing in response to a signal generated by said sensor, wherein the at least some of the stimuli are tactile stimuli, and wherein the timing of the tactile stimuli is selected so as to prompt the subject to exhale sufficiently to meet a target. In some embodiments the target comprises exhaling at least a specified volume or for at least a specified period of time. In some embodiments the apparatus comprises a controller that determines an appropriate stimulus, based at least in part on analyzing the subject's breathing over one or more preceding breathing cycles.

In some aspects the invention provides an abdominal muscle stimulating belt comprises a respiratory effort sensor. In some embodiments an abdominal muscle stimulating belt comprises a respiratory effort sensor comprising a piezoelectric sensing element. In some embodiments the respiratory effort sensor is an integral part of the abdominal muscle stimulating belt.

In some aspects, the invention provides a method of promoting increased abdominal muscle strength in a subject, the method comprising: (a) sensing when a subject is inhaling; and (b) stimulating contraction of at least one of the subject's expiratory muscles during at least part of the inhalatory phase of breathing in response to said sensing. In some embodiments the subject suffers from an obstructive respiratory disorder.

In some aspects the invention provides a method of assisting breathing of a subject in need thereof, the method comprising steps of: (a) sensing when a subject is exhaling; and (b) delivering a tactile stimulus to the subject during at least part of the expiratory phase of breathing in response to said sensing, wherein the tactile stimulus serves as a cue to assist the subject with timing the contraction of the subject's expiratory muscles. In some embodiments the subject has been instructed to continue exhaling or contracting the exhalatory muscles while he or she continues to feel the stimulus. In some embodiments the method comprises determining an appropriate stimulus to be delivered during an exhalation, based at least in part on analyzing the subject's breathing over one or more preceding breathing cycles. In some embodiments the method comprises determining whether to deliver a tactile stimulus or a stimulus that stimulates contraction of one or more expiratory muscles during an exhalation, based at least in part on analyzing the subject's breathing over one or more preceding breathing cycles. In some embodiments the subject suffers from COPD.

All articles, books, patent applications, patents, other publications, websites, and databases mentioned in this application are incorporated herein by reference. In the event of a conflict between the specification and any of the incorporated references the specification (including any amendments thereto) shall control. Unless otherwise indicated, art-accepted meanings of terms and abbreviations are used herein. The term "exhalation" is used interchangeably with "expiration", "expiratory phase of breathing", or "breathing out". The term "inhalation" is used interchangeably with "inspiration", "inspiratory phase of breathing", or "breathing in". Section headings herein are for convenience only and should not be understood to limit the invention.

Non-limiting information regarding risk factors, epidemiology, pathogenesis, diagnosis, and management of COPD may be found, e.g., in "Global Strategy for the Diagnosis, Management, and Prevention of Chronic Obstructive Pulmonary Disease" (updated 2009) available on the Global Initiative on Chronic Obstructive Pulmonary Disease, Inc. (GOLD) website (www.goldcopd.org), also referred to herein as the "GOLD Report", the American Thoracic Society/European Respiratory Society Guidelines (2004) available on the ATS website at www.thoracic.org/clinical/copd-guidelines/resources/copddoc.pdf, referred to herein as "ATC/ERS Guidelines" and standard textbooks of internal medicine such as Cecil Textbook of Medicine (20th edition), Harrison's Principles of Internal Medicine (17th edition), and/or standard textbooks focusing on pulmonary medicine.

DETAILED DESCRIPTION OF CERTAIN EMBODIMENTS OF THE INVENTION

Figure 1:
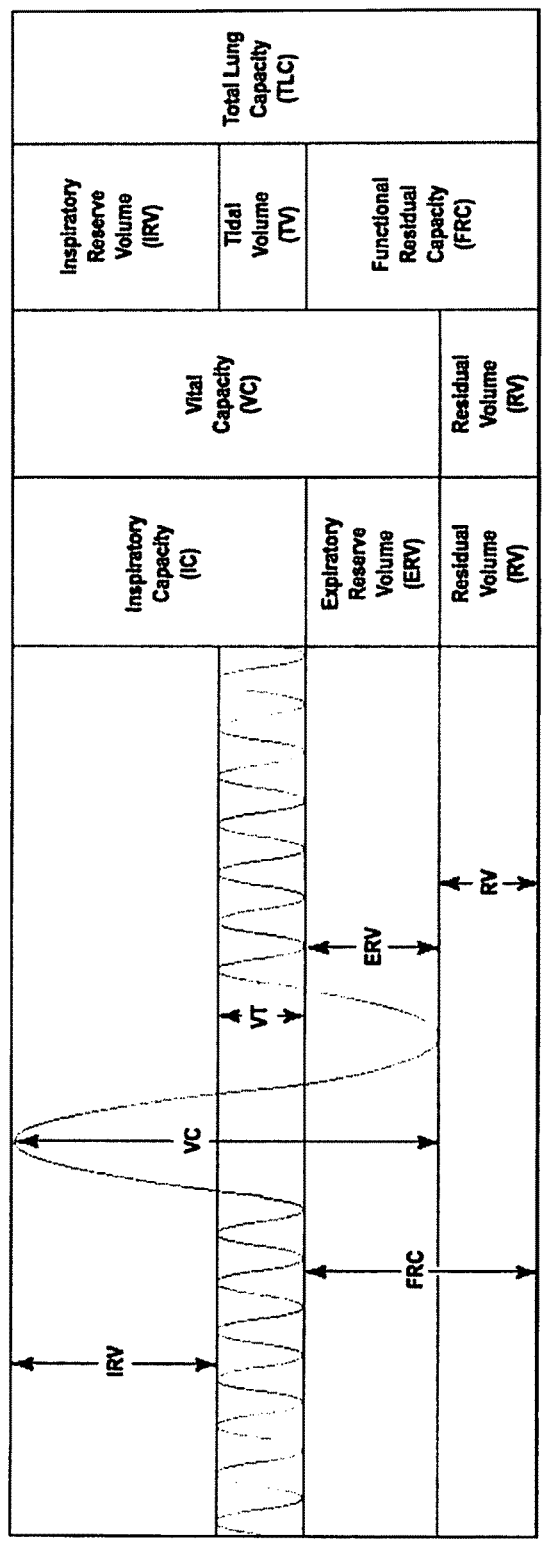
FIG. 1 is a diagram illustrating various lung volumes and capacities associated with breathing. Definitions and information regarding methods useful for measuring these volumes and capacities are found, e.g., in the ATS/ERS Task Force Standardisation of Lung Function Testing: Standardisation of the measurement of lung volumes (2005).

The present invention provides apparatus and methods of use for assisting the breathing of individuals suffering from obstructive respiratory diseases. Obstructive respiratory diseases are disorders in which air flow limitation is a prominent and defining feature. Chronic obstructive pulmonary disease (COPD) encompasses a spectrum of conditions characterized by airflow limitation that is not fully reversible even with therapy and is usually progressive. Symptoms of COPD include dyspnea (breathlessness), decreased exercise tolerance, cough, sputum production, wheezing, and chest tightness. Persons with COPD can experience episodes of acute (e.g., developing over course of less than a week and often over the course of 24 hours or less) worsening of symptoms (termed COPD exacerbations) that can vary in frequency and duration and are associated with significant morbidity. They may be triggered by events such as respiratory infection, exposure to noxious particles, or may have an unknown etiology. Smoking is the most commonly encountered risk factor for COPD, and other inhalational exposures can also contribute to development and progression of the disease. The role of genetic factors in COPD is an area of active research. A small percentage of COPD patients have a hereditary deficiency of alpha-1 antitrypsin, a major circulating inhibitor of serine proteases, and this deficiency can lead to a rapidly progressive form of the disease.

Characteristic pathophysiologic features of COPD include narrowing of and structural changes in the small airways and destruction of lung parenchyma (in particular around alveoli), most commonly due to chronic inflammation. The chronic airflow limitation observed in COPD typically involves a mixture of these factors, and their relative importance in contributing to airflow limitation and symptoms varies from person to person. The term "emphysema" refers to enlargement of the air spaces (alveoli) distal to the terminal bronchioles, with destruction of their walls. It should be noted that the term "emphysema" is often used clinically to refer to the medical condition associated with such pathological changes. Some individuals with COPD have chronic bronchitis, which is defined in clinical terms as a cough with sputum production on most days for 3 months of a year, for 2 consecutive years. Asthma is another obstructive respiratory disorder, however the obstruction is usually (at least initially) reversible, i.e., with therapy and/or between asthma "attacks" airflow through the airways of persons with asthma is typically normal, and thus these individuals do not have COPD. However, particularly if asthma is left untreated, the chronic inflammation associated with the disease can lead to airway remodeling, causing the airway obstruction to become at least in part irreversible so that the asthmatic patient may then have abnormal air flow even between attacks. Thus asthmatic individuals with a fixed component of airway obstruction are considered to have COPD.

Figure 2:
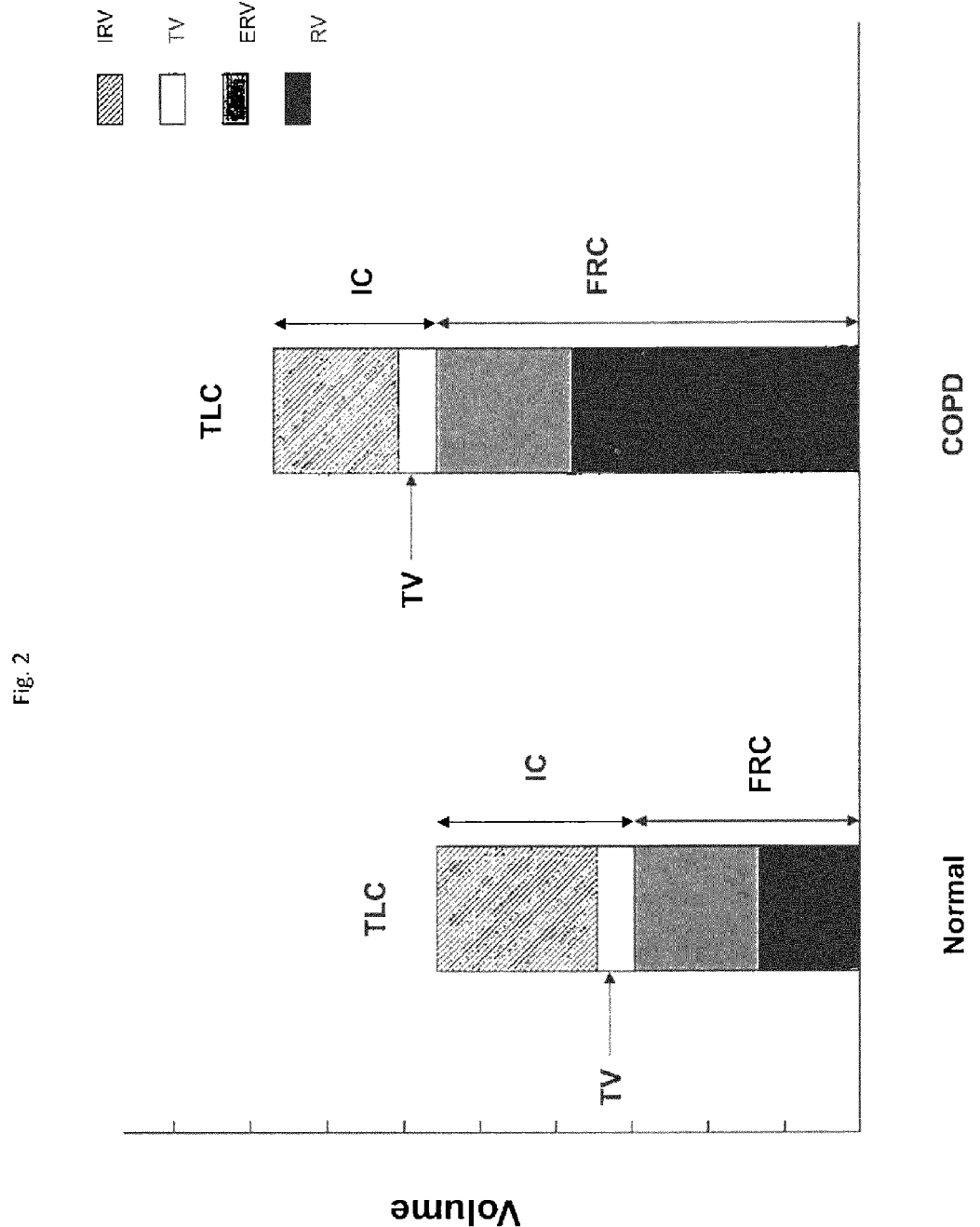
FIG. 2 is a graph that shows static respiratory volumes and capacities illustrative of a healthy adult human (left) and an adult human with COPD (right). It will be understood that there is variability both among healthy individuals and persons with COPD.

The pathophysiologic changes that take place in COPD have a variety of deleterious effects on ventilation (movement of air into and out of the lungs) and the mechanics of breathing. Loss of alveolar walls and attachments to the small airways decreases lung elastic recoil. Decreased elastic recoil, together with airway narrowing, reduces the ability of the airways to remain open during exhalation. Thus the airways tend to collapse earlier during exhalation. The collapse of small airways during exhalation impedes airflow (sometimes referred to as "expiratory flow limitation" (EFL)), and as a result air becomes trapped in the lungs leading to lung hyperinflation. Hyperinflation is considered to be present when gas volume in the lung(s) is increased as compared with the predicted value for age-matched, healthy individuals. In particular, patients with COPD have a significantly increased end-expiratory lung volume as compared with healthy controls, which may result in an increased total lung capacity (TLC) (see FIG. 2). As known in the art, "end expiratory lung volume" (EELV) (which term is used interchangeably herein with "functional residual capacity" (FRC)) refers to the volume of gas remaining in the lungs after passive expiration. EELV can be measured as known in the art, e.g., using the helium dilution technique, single or multiple breath nitrogen washout test, body plethysmography, radiographic planimetry, CT scan, or other suitable methods. The negative expiratory pressure (NEP) technique can be used for the diagnosis or assessment of EFL. Using this method, the degree of EFL present is evaluated by examining the proportion of the expiratory phase over which airflow rate is unchanged when a small negative pressure is applied at the mouth. This technique has several scales of measurement, including a 3 point scale, a 5 point scale, and a continuous scale.

Tidal volume (TV) frequently remains relatively normal in persons with COPD, but tidal breathing takes place at greater lung volumes than normal (see FIG. 2) as a result of the increase in EELV. The residual volume (RV), the volume of air left in the lungs following full expiration, is often increased in COPD, as is the total lung capacity, while the vital capacity remains relatively normal. Hyperinflation may be reflected by various signs on physical examination, e.g., relatively horizontal ribs, "barrel-shaped" chest, protruding abdomen. Static hyperinflation refers to hyperinflation that occurs at rest and often becomes more pronounced as COPD progresses. Dynamic hyperinflation refers to acute and variable increase in hyperinflation (e.g., as reflected by EELV) above its baseline value and may occur, e.g., during exercise and COPD exacerbations. It may be assessed by measuring the inspiratory capacity (IC).

COPD can lead to a variety of changes in the mechanics of breathing. Under normal physiologic conditions in healthy individuals, inspiration is an active process while expiration is passive during rest. The diaphragm is the most important muscle of inspiration. It moves downward upon contracting, forcing the contents of the abdomen downward and forward and causing the vertical dimension of the chest cavity to increase. In addition, the ribs are lifted upwards and outwards causing the rib cage to widen. The external intercostal muscles, which connect adjacent ribs, also function in inspiration by pulling the ribs upward and forward, thus contributing to increasing the dimensions of the thorax. The increase in thoracic dimensions creates negative pressure within the lungs, resulting in air inflow. Due to their elasticity, in healthy individuals under normal physiologic conditions the lung and chest wall return to their equilibrium positions after the expansion that takes place during inspiration. Thus exalation occurs passively. During exercise or other situations in which increased breathing is required, exhalation is an active process involving contraction of at least some of the muscles of expiration, e.g., the internal intercostal muscles, abdominal muscles (rectus abdominis, external oblique, internal oblique, thoracis abdominis). In persons with COPD, expiration increasingly comes to depend on the expiratory muscles, particularly in the end expiratory phase. In addition, the increase in EELV that occurs in COPD requires the muscles of inspiration (diaphragm and external intercostals) to operate at a higher volume than would otherwise be the case. "Intrinsic" positive end-expiratory pressure (PEEPi), also called auto PEEP, is often increased in persons with COPD and constitutes an inspiratory threshold load on the respiratory muscles, increasing work of breathing. Thus, for a variety of reasons, patients with COPD often expend considerably more effort and energy in breathing than healthy individuals.

The present invention encompasses the recognition that obstructive respiratory diseases can be treated by applying a stimulus to the lower thorax and/or the abdomen of a subject during the expiratory phase of breathing. Lower thorax refers to the region of the thorax at or below the $7^{th}$ intercostal space. In some aspects, the invention features delivering a stimulus to the lower thorax and/or abdomen of a subject with an obstructive respiratory disease, wherein the stimulus is effective to assist the subject with exhalation. In some aspects, the invention provides a method comprising sensing when a subject (e.g., a subject with an obstructive respiratory disorder), is exhaling and delivering a stimulus to the subject's lower thorax or abdomen based at least in part on the sensing. In many embodiments, the stimulus is delivered to the lower anterior thorax and/or to the abdomen. In particular embodiments, the stimulus is delivered to at least some abdominal muscles. In some aspects, the inventive method reduces the subject's EELV. The invention provides a method comprises sensing when a subject (e.g., a subject with an obstructive respiratory disorder) is exhaling and delivering a stimulus to the subject. Thus the inventive method comprises delivering a stimulus "in synchrony" or "in phase" with a subject's exhalation based on sensing one or more indicators of the subject's breathing. In some embodiments, the stimulus is effective to assist the subject with exhaling. In some embodiments the stimulus is effective in training the expiratory muscles in order to gain strength and endurance. In some embodiments a feedback system between a sensor (sensing when the patient is exhaling) and the muscle stimulation stimulus teaches the patient to use the proper muscles to assist in expiration.

As described further herein, the invention also provides, in some aspects, apparatus suitable for use in one or more methods of the invention. Thus in one aspect, the invention provides an apparatus comprising: (a) a sensor suitable for detecting when a subject is exhaling; and (b) a device adapted to deliver a stimulus to the subject's thorax or abdomen during at least part of the expiratory phase of the subject's breathing in response to a signal generated by said sensor. In some embodiments, the apparatus comprises a sensor and a stimulus device that are integrated or readily integrable into a single unit, such as a belt, that is wearable around the waist of a subject. Both (a) and/or (b) can be implantable or placed on the surface of the skin.

In some embodiments, the inventive method augments the natural action of the muscles of exhalation by stimulating them electrically or magnetically or by delivering a mechanical stimulus to the lower anterior thorax and/or abdomen. In some embodiments, an electrical stimulus delivered to muscle(s) of expiration and/or to motor nerve(s) that supply those muscle(s) will increase the force of contraction during expiration as compared with the force that would be generated in the absence of the stimulus. The electrical stimulus may, for example, cause recruitment of a greater number of motor units of one or more expiratory muscles than would be stimulated as a result of a subject's typical motor nerve impulse and/or cause contraction of one or more muscle(s) or portion(s) of one or more muscle(s) that would otherwise not substantially contract. Without wishing to be bound by any theory, in some embodiments an electrical stimulus may serve to automatically stimulate muscles that are under voluntary control; thus the subject will not need to exert volitional control in order to cause such muscle(s) to contract. A mechanical stimulus can comprise mechanical compression of the lower anterior thorax and/or abdomen, causing an increase in intrathoracic pressure and, in at least some embodiments, thereby assisting exhalation.

In some embodiments of the invention, the effect of the stimulus is to shift the volume at which tidal ventilation occurs downward. One aspect of the invention is the recognition that inhaling at lower lung volumes may reduce stress on the muscles of inspiration, and thus a stimulus delivered to muscles of exhalation has the potential to improve inspiration. For example, hyperinflation necessitates breathing over higher ranges of the lung volume where the inspiratory muscles are functionally weaker. Hyperinflation depresses the dome of the diaphragm. In some aspects, use of an inventive apparatus reduces such depression of the diaphragm. Use of an inventive apparatus may, by reducing hyperinflation, allow the fibers of inspiratory muscle(s), e.g., the diaphragm, to operate within a more optimal portion of their length-tension relation. The inventive method may reduce inspiratory and/or expiratory muscle fatigue in patients with COPD. In patients with COPD air trapping in the lungs increases greatly during exercise as patients breath more rapidly, reducing the time available for exhalation and/or causing patiets to start inhaling before full exhalation is achieved. The inventive method may reduce this dynamic hyperinflation, e.g., by causing air to exit the lungs more rapidly during at least part of exhalation than would otherwise be the case and/or by reducing the subject's EELV that exists at the start of exercise.

A feature of certain aspects of the invention is that the stimulus (whether electrical or mechanical) is appropriately timed in relation to the subject's natural expiration so as to result in one or more benefits to the subject. Without limiting the invention in any way, the stimulus may result in (a) a decreased EELV as compared with the subject's EELV in the absence of the stimulus and/or (b) an increased expiratory flow rate during at least a portion of exhalation than would be the case in the absence of the stimulus. However, the stimulus preferably does not make inhalation significantly more difficult for the subject. In at least some embodiments, the stimulus does not increase the work associated with inspiration and/or does not make inspiration feel subjectively more difficult for the subject. In some embodiments, the stimulus actually makes inhalation easier for the subject, e.g., it reduces stress on at least some muscles during inhalation and/or makes inhalation feel subjectively easier for the subject. The inventive method, in some embodiments, avoids stimulating the muscles of expiration or mechanically compressing the anterior lower thorax or abdomen while the subject is inhaling (or any such stimulus is below the threshold level required to produce significant muscle contraction or compression during inhalation) and/or avoids significantly stimulating the muscles of inspiration while the subject is exhaling (or any such stimulus is below the threshold level required to produce significant contraction of the muscles of inspiration during exhalation). In many embodiments, the muscles of inspiration are not stimulated during either exhalation or inspiration (or any such stimulus is below the threshold level required to produce significant contraction of the muscles of inspiration). However, as described herein, without wishing to be bound by any theory, the subject may benefit during inhalation as well. The inventive method may or may not result in an alteration in the subject's average EELV as compared with the the subject's average EELV in the absence of the stimulus. The inventive method may or may not result in an alteration in the subject's average TV as compared with the the subject's average TV in the absence of the stimulus. The inventive method may or may not result in an alteration in the subject's average respiratory rate (RR). For example, some persons suffering from an obstructive lung disease such as COPD take frequent, shallow breaths in an effort to compensate for the condition. The inventive method may restore a more normal breathing pattern in such persons (e.g., higher TV and lower RR). In other persons suffering from an obstructive lung disease, the average resting TV and RR may be approximately normal (normal resting TV is often estimated at about 500 ml and normal resting RR is often estimated at about 12-20 per minute, for adult humans), and the inventive method may not significantly affect these values.

An inventive method may be applied for varying periods of time. Such time period may be referred to as a "session". For example, and without limitation, a session may last between about 30 minutes and about 12 hours. In some embodiments, a session lasts between 1 and 6 hours. In some embodiments, a session lasts for between 1 minute and 30 minutes. In some embodiments a session comprises multiple subsessions in which stimuli effective to enhance expiratory muscle contraction are delivered over a relatively short time period, e.g., from 1-5 or 5-10 minutes, alternating with time periods during which stimuli effective to enhance exhalatory muscle contraction are not delivered. The length and/or number of subsessions and/or time periods between subsessions may independently vary. As but one example, 6 subsessions, each lasting 5 minutes, may be applied over a session lasting 1 hour, with 5 minute periods between subsessions. In some embodiments, the length and/or number of subsessions and/or time periods between subsessions are predetermined prior to the beginning of a session. In some embodiments, the length and/or number of subsessions and/or time periods between subsessions are at least in part determined by the apparatus during a session based at least in part on input from a sensor that provides information regarding the subject's respiration or physical activity. Without limiting the invention in any way, it is noted that at least some beneficial effects may occur gradually after the stimulus has been applied over a number of breaths as, for example, trapped air is slowly forced out of the lungs over a period of time. Thus one or more benefits may only become evident some time after a particular session has begun. Furthermore, without wishing to be bound by any theory, at least some beneficial effects may last for a period of time after the stimulus is no longer being applied (i.e., after the end of a particular session). In other words, the subject may experience a period of continued benefit without continued application of the stimulus. In some embodiments, sessions are timed sufficiently close together that the subject's condition remains at least somewhat improved during the time period between sessions. It should be understood that the invention does not depend on results achieved, which may reasonably be expected to vary among different subjects.

The timing of delivery of the stimulus within the respiratory cycle and its characteristics, e.g., duration and strength, may vary. For example, one or more of these parameter(s) may be selected so that increased contraction of one or more muscle(s) of expiration or increased compression of the lower anterior thorax and/or abdomen will occur mainly during the first half or mainly during the second half of the expiratory phase. In some embodiments, the stimulus is delivered during each respiratory cycle, while in other embodiments the stimulus may be delivered less frequently, e.g., every second, third, fourth, or fifth breath, or successive stimuli delivered according to a stimulus protocol may be separated by different numbers of breaths. In some embodiments, stimulation is delivered between 12-20 times per minute, between 6-12 times per minute, or between 3 and 6 times per minute. In some embodiments, the stimulus may be delivered substantially throughout exhalation or during only a portion of the expiratory phase of breathing, e.g., during the first or second half of an exhalation. In some embodiments the delivery of the stimulus begins a predetermined amount of time after the end of inspiration or a predetermined amount of time after the onset of exhalation. The stimulus may be delivered during one or more time intervals during an exhalation, which time intervals may be separated by intervals in which the stimulus is not delivered. Furthermore, the magnitude of the stimulus may vary continuously or discretely during such time interval(s). Parameters can be selected, e.g., to optimize or enhance comfort and/or efficacy for a particular subject or situation (e.g., exercise vs rest; awake vs asleep). In some embodiments, an electrical or magnetic stimulus is not delivered to expiratory muscle(s) or to efferent nerves supplying them during inspiration (or the magnitude of any electrical or magnetic stimulus delivered during inspiration is not sufficient to cause contraction of the muscle(s) of expiration) and the lower anterior thorax and abdomen are not mechanically compressed during inspiration.

In some embodiments, the method comprises providing means by which an individual can control at least aspects of the stimulus. For example, an inventive apparatus may have a control device that allows an individual (e.g., the subject, a caregiver, etc.) to switch the apparatus on or off and/or to select particular settings. The apparatus may have multiple pre-programmed settings that permit one or more parameter(s) or combinations of parameters for the stimulus to be selected by an individual based, e.g., on personal preference, comfort, therapeutic goals, and/or activity level. Examples of situations in which different stimulus parameters and/or signal conditioning procedures may be used include, e.g., sleeping, quiet breathing while awake (e.g., in any of various postures such as lying down, sitting, or standing), mild exercise that has a regular pattern (e.g., walking with few or no interruptions), mild exercise that has an irregular pattern (e.g., activities during which the subject starts and stops walking or moving, e.g., relatively often or at unpredictable times), etc. In some aspects, an apparatus or method disclosed herein selects stimulus parameters and/or signal conditioning procedures based at least in part a subject's breathing pattern, posture, and/or physical activity pattern. In some aspects, an apparatus or method disclosed herein applies stimulus parameters and/or signal conditioning procedures selected based at least in part on a subject's breathing pattern, posture, and/or physical activity pattern. As described further below, in some embodiments an apparatus is capable of distinguishing between different breathing patterns, postures, and/or physical activity patterns based at least in part on input from one or more sensors. In some embodiments a method comprises distinguishing between different breathing patterns, postures, and/or physical activity patterns based at least in part on analyzing input from one or more sensors and, in some embodiments, delivering an appropriate stimulus based at least in part on such analysis The apparatus may be programmable so that parameters for delivering the stimulus can be customized for a particular subject and stored, so that a user will be able to conveniently select that combination of parameters in the future. In some embodiments the apparatus comprises means for receiving and/or responding to a voice input. For example, the apparatus may comprise or access voice recognition software. In some embodiments instructions (e.g., turning on and off, selecting a particular stimulation protocol, etc.) may be given to the apparatus at least in part orally.

The inventive apparatus and methods may be implemented using a variety of different components, which may be combined in a variety of different ways. One aspect of the invention lies in the linking of various components (e.g., sensor, stimulus device), e.g., by means of an appropriate interface, so that the apparatus as a whole will function as described herein. Appropriate electronics to interface a sensor suitable for sensing when a subject is exhaling and a device for providing a stimulus are an aspect of the invention. An interface may be implemented using hardware, software, or a combination of hardware and software, and may comprise analog and/or digital components. Appropriate signal processing and analysis functionality may be provided. An interface may comprise one or more electronic components such as one or more amplifiers, filters, rectifiers, peak detector(s), switches, analog to digital converter, connectors (e.g., DIN, XLR, etc.), wires, cables, etc. In some embodiments an apparatus comprises, e.g., as part of the interface, a signal conditioning unit. In some embodiments a signal conditioning unit comprises one or more amplifiers and one or more filters. Amplifier(s) may, for example, provide a signal amplification gain of 1000 to 5000 in some embodiments. In some embodiments an apparatus comprises, e.g., as part of a signal conditioning unit, one or more high pass filter(s) and/or one or more low pass filter(s). The high pass filter(s) may, for example, have a cut-off frequency in the region of 0 Hz to 1 Hz. The low pass filter(s) may have, for example, a cut-off frequency in the region of 10 Hz to 70 Hz. Such filter(s) may be of use, e.g., to eliminate or reduce noise or other artifacts. In some embodiments different signal conditioning procedures may be utilized according to the setting. For example, different signal conditioning procedures may be used to detect or eliminate movement artifacts if a subject is walking, breathing quietly while awake, sleeping, etc.

Figure 3:
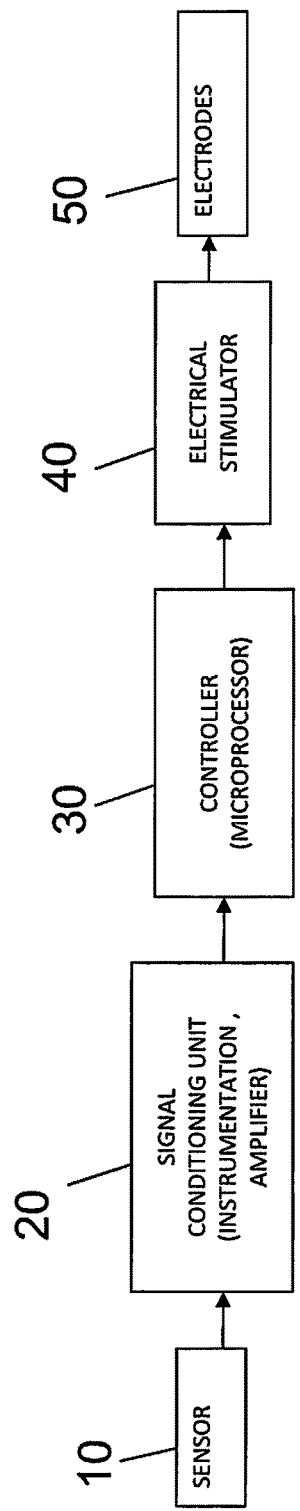
FIG. 3 is a block diagram of an apparatus for providing electrical stimulation to expiratory muscles of a subject, e.g., in synchrony with exhalation.

FIG. 3 shows an exemplary block diagram of an apparatus in certain embodiments. As depicted in FIG. 3, an exemplary apparatus comprises sensor 10, which provides an input to signal conditioning unit 20. Signal conditioning unit 20 processes the signal (e.g., using instrumentation such as an amplifier, filter(s), etc.). The processed signal serves as input to controller 30. Controller 30 analyzes the signal, determines whether and when to provide an output to electrical stimulator 40, and delivers an output to electrical stimulator 40 as appropriate. Electrical stimulator 40 generates an electrical stimulus which is delivered to a subject via electrode(s) 50. In some embodiments control unit 30 receives additional inputs, such as from a user control unit (not depicted in FIG. 3) or from one or more additional sensor(s) or signal conditioning unit(s) that process signals from such sensor(s) (not depicted in FIG. 3). For example, in some embodiments controller 30 receives an input from a user control unit that selects one or more stimulus parameters or selects a particular stimulus protocol or stimulus mode. In some embodiments controller 30, in addition to providing input to electrical stimulator 40, provides input to one or more devices such as a computer, display, data storage unit, electronic transmission device, etc.

Materials, components, and parts for use in an apparatus of the invention may be selected to provide a comfortable, relatively light-weight, portable apparatus that can be used conveniently by a subject. In some embodiments, materials, components, and parts may be selected such that the total weight of the apparatus is less than or equal to about 0.5 kg-2 kg. In some embodiments, the apparatus is wearable and sufficiently light such that, in at least some embodiments, the subject can carry out most activities of daily living while using the device. In some embodiments, the apparatus is simple and convenient for a subject to put on and use, so that the subject can employ the apparatus with minimal or no assistance.

In some embodiments, the apparatus of the invention collects, stores, analyzes, displays, and/or transmits physiological data from the subject in addition to providing the exhalation sensing and stimulus delivery functions described herein. The inventive apparatus may, in some embodiments, be used to sense various characteristics of the subject's breathing (in addition to the sensing required to determine when the subject is exhaling) and/or to detect or measure other physiological variable(s) or events such as heartbeat, blood pressure, oxygen saturation, temperature, etc. The apparatus may, for example, detect, collect, optionally analyze, store, and/or transmit, breathing frequency, tidal volume, work of breathing, events such as coughing, and/or any other physiological variable(s) or event(s) of interest. The information may, for example, be stored in the apparatus, downloaded to a computer or data storage device, and/or transmitted to a remote location (e.g., wirelessly) either directly by the apparatus or by said computer. In some embodiments, technology used in the LifeShirt® (VivoMetrics; Ventura, Calif.) is used or modified for use in apparatus of the invention, e.g., for purposes of sensing, data collection, and/or data transmission. The apparatus may provide useful monitoring of health-related variables (e.g., cardiac parameters) in addition to assisting the subject with breathing. The remote location may be, e.g., a facility where staff are available to assess the data and/or to respond to or initiate an alert, a data storage center, etc. An electronic transmission may occur over a communications network, e.g., the Internet. In some embodiments a remote location is at least 1 km away.

A "computer" in the context of the present invention can be, e.g., a smartphone, personal digital assistant, personal computer (which may be laptop, desktop, notebook, or tablet computer), etc. Optionally, an apparatus of the invention interfaces with a computer that may comprise or be connected to a display, keyboard, mouse, or other peripherals. Optionally, information indicative of breathing and/or indicative of operation of an inventive apparatus can be visually displayed. For example, waveforms associated with breathing may be displayed and/or stimulus parameters may be displayed. In some embodiments, one or more lung volumes or capacities, work of breathing, respiratory movement or effort reported by a sensor, and/or respiratory rate, or any physiological variable of interest, may be displayed. The invention thus provides a system comprising any apparatus as described herein and a computer that communicates with the apparatus either through a physical connection or wirelessly.

Non-limiting descriptions of exemplary materials, components, parts, and implementation approaches that may be used in inventive apparatus and/or methods are described herein, e.g., in the sections below. It should be understood that the invention encompasses use of different materials, components, parts, and/or means of implementation. Components, parts, materials, etc. may be freely combined in any reasonable combination, and the resulting apparatus and methods of use thereof are within the scope of the invention. In some aspects, the invention encompasses the modification of various components or parts, e.g., commercially available components or parts, to facilitate their use in an apparatus and/or method of the invention. Such modified components or parts are aspects of the invention.

Methods and Sensors for Sensing Exhalation

A variety of approaches and sensor types may be used to sense when a subject is exhaling. In general, a sensor of use in the present invention detects any of a variety of physical quantities that vary during breathing and generates a signal, typically an electrical signal, indicative of the magnitude of the physical quantity and/or indicative of a rate of change in the magnitude of the physical quantity. Thus the sensor may comprise a detecting or sensing element and a transducing element, wherein the transducing element converts, e.g., mechanical energy into electrical energy and provides an output signal in the form of a voltage or current. Such element(s) may be located at least in part in a suitable housing, which may be composed, for example, at least in part of a fabric, plastic, or other suitable material. The housing may provide means for attaching the sensor to a component of the apparatus or to a subject. In some embodiments the sensors may be implantable and sense one or more characteristics intracorporeally (for example by sensing intra-abdominal pressure) Implantable element(s) and/or their housing may be made at least in part of biocompatible materials suitable for implantation. Descriptions herein of various modalities and sensors available for sensing breathing are not intended to conflict with the understanding of those of ordinary skill in the art and should not be interpreted to limit the invention.

In some embodiments of the invention, air flow is measured using, e.g., one or more pressure and/or temperature sensors. For example, a thermal sensor (which may comprise a thermistor or pyroelectric material (e.g., pyroelectric crystal)) generates a signal based on temperature changes driven by the warm air of exhalation and the comparatively cool air of inhalation passing over the sensor and can be used to determine when a subject is exhaling. A pressure-based airflow sensor generates a signal in response to changes in pressure produced by inhalation and exhalation and likewise can be used to determine when a subject is exhaling. Pressure and/or temperature sensors may be placed nasally or orally.

In some embodiments, a change in one or more dimension(s) of the thorax or abdomen as an individual exhales and/or inhales is detected. Dimension(s) may include one or more of the three main dimensions of the chest: anteroposterior, transverse and vertical. Such measurements thus can detect movement associated with inhalation/exhalation and/or change in volume of the thorax and/or abdomen that occurs with breathing. A sensor may comprise piezoelectric, optical waveguide, and/or electroconductive materials. For example, the sensor may be a piezoelectric sensor that uses the piezoelectric effect to measure strain or pressure and convert it to an electrical signal. A piezoelectric sensor can be fabricated as known in the art using, e.g., piezoelectric ceramics or single crystal materials. Such sensors may be used to measure air flow and/or respiratory movement. A piezo-electric sensor comprising a crystal outputs a signal when the crystal is compressed or stretched, generating a voltage. In some embodiments, a piezoelectric sensor comprises a polymer with piezoelectric properties. The polymer may be provided as a film. For example, in some embodiments, polyvinylidene fluoride (PVDF), e.g., as a PVDF film, is used as a sensing element in a piezoelectric sensor. In some embodiments a piezoelectric sensor represents changes in volume indirectly by capturing strain in an elastic band or belt that is transferred to a piezo sensor. Such a belt or band is fastened around the chest or abdomen to measure changes in tension during breathing. Other types of strain gauges could be used as a sensor. Electroconductive fibers may be used as a sensing element, which may be incorporated into electroconductive strips or bands. In some embodiments, a change in dimension(s) of the chest causes a change in the resistance of the electroconductive strips or bands. In some embodiments, a change in dimension(s) of the chest causes a change in inductance of the electroconductive strips of bands.

Piezoelectric sensors that may be used for sensing breathing, and materials of use in such sensor(s) are described, e.g., in U.S. Pat. No. 6,383,143; PCT application publication WO/2008/136980, and references therein. Piezo respiratory effort sensors and bands available from Philips Respironics (Murrysville, Pa.) or Scientific Laboratory Products, Ltd. (SLP) (St. Charles, Ill. and Tel-Aviv, Israel) or Dymedix, Inc. (Shoreview, Minn.) may be used. For example, in some embodiments, the SleepSense™ Piezo Crystal Respiratory Effort Kit (product no. 1370) available from SLP or a PerfectFit™ Effort Belt available from Dymedix, Inc., or a P1420 or P1460 or similar Piezo respiratory effort sensor available from Philips Respironics is used.

Techniques for sensing breathing (and determining when a subject is exhaling) include inductive plethysmography and impedance plethysmography. Inductance plethysmography comprises measurement based on inductance or mutual inductance of conductive elements placed around a body part of a subject, e.g., around a subject's chest and/or abdomen. Respiratory inductive plethysmography (RIP) in some aspects of the invention utilizes the principle that a changing (e.g., oscillating) current applied through loops of wire generates a magnetic field. Appropriate wires are placed around the subject's chest and/or abdomen (often about both the chest and abdomen) and a signal is sent through the wires. One or more characteristics of the signal (e.g., its frequency) is altered as a result of the movements of breathing as they change the area enclosed the wires. The alteration in the signal is representational of the change in area that occurs with breathing and can be used to determine, among other things, when a subject is exhaling. A RIP sensor can, for example, generate a signal representing changes in tidal volume over time. A plateau in TV or beginning of a decrease in TV occurs as exhalation begins. RIP sensors are well known in the art. See, e.g., U.S. Pat. Nos. 5,131,399; 5,913,830; PCT application publications WO/2001/003581; WO/2006/03429, etc. The wires of a RIP sensor are typically contained within belts or bands, in some embodiments, encircle the rib cage and abdomen at about the level of the nipples and the umbilicus. The bands or belts may be between about 1-5 cm wide in certain embodiments. They may at least in part be composed of a stretchable material or may comprise a section composed of a stretchable material to permit close fitting. In some embodiments, a RIP sensor comprises two sinusoid wire coils insulated and placed within two approximately 2.5 cm (about 1 inch) wide, lightweight elastic and, optionally, adhesive bands. The transducer bands are placed around the rib cage under the armpits and around the abdomen at the level of the umbilicus. They are connected to an oscillator and subsequent frequency demodulation electronics to obtain digital waveforms. During inspiration the cross-sectional area of the rib cage and abdomen increases, altering the self-inductance of the coils and the frequency of their oscillation, with the increase in cross-sectional area proportional to lung volumes. The electronics convert this change in frequency to a digital respiration waveform where the amplitude of the waveform is proportional to the inspired breath volume.

RIP sensors available from Philips Respironics or Scientific Laboratory Products (SLP) may be used in the inventive apparatus. For example, zRTP DuraBelt inductance respiratory effort sensors (Philips Respironics) or SleepSense® sensors (SLP) may be used.

In some embodiments of the invention, position sensor feedback is used, e.g., to adjust calibration of a respiratory sensor, e.g., an RIP sensor, e.g., after the subject changes position.

In some embodiments, impedance plethysmography is used to sense when a subject is exhaling.

The apparatus can comprise multiple sensors (e.g., 2, 3, 4, 5, or more), which can be of the same or different types (e.g., RIP and piezoelectric). The signals generated by the multiple sensors may be analyzed to improve the accuracy of determining when a subject is exhaling (as compared with the accuracy obtained with a single sensor). For example, in some embodiments multiple sensor(s) must generate a signal indicative of exhalation in order to trigger delivery of the stimulus.

In some embodiments, a sensor is equipped with means that permit integration with or reversible attachment to a garment or belt.

In certain embodiments, one or more implanted sensor(s) is used. The sensor(s) may directly detect action potentials or muscle contractions in some embodiments.

It should be understood that "sensing when a subject is exhaling" is used in a broad sense to encompass any appropriate method of determining an appropriate time to deliver the stimulus (e.g., within a particular respiratory cycle consisting of an inhalation and an exhalation), e.g., so as to assist at least with exhalation. In some embodiments, the apparatus senses the onset of exhalation. For example, a change from inhaling to exhaling may be detected by detecting a change from inward to outward flow of air and/or by detecting that one or more dimensions of the thorax that had been increasing has reached a plateau or is decreasing. It will be appreciated that the event(s) or phenomena that are detected to determine when a subject is exhaling may occur during inspiration. For example, as inspiration comes to an end during each breath, the inspiratory flow rate and rate of expansion of the thorax typically decline. A decline in inspiratory flow rate and/or rate of expansion of the thorax may be detected and serve as a means to determine that the expiratory phase of breathing will occur within a short time thereafter. It will also be understood that the different sensing modalities may not produce identical results, e.g., as compared with results that would be obtained using spirometry. The invention encompasses variations in the absolute timing of delivery of the stimulus that would result from use of different sensing modalities, e.g., as compared with the timing that would result if spirometry were used to determine when a subject is exhaling.

Electric or Magnetic Stimulus and Stimulus Device

In some embodiments, the apparatus delivers an electric or magnetic stimulus to at least some of the expiratory muscles so as to elicit muscle contraction. Expiratory muscles of interest include the rectus abdominis, external oblique, internal oblique, and transversus abdominis. (It will be understood that an electrical or magnetic stimulus may be delivered to a portion of one or more muscle(s). In other words, the stimulus may be applied only to a portion of a muscle or muscle(s) rather than the entire muscle.)

In some embodiments, the device employs electrical muscle stimulation, which is well known in the art. EMS elicits muscle contraction using electric impulses. The impulses are generated by the device and delivered through electrodes positioned in close proximity to the muscle(s) to be stimulated and/or in close proximity to efferent nerve(s) that supply such muscle(s). For example, the electrodes may be positioned on the skin and may directly overly the muscle(s) to be stimulated. The device causes muscles to contract (typically repeatedly) by applying pulsed electric current through the cutaneous electrodes. EMS is used for various purposes such as in physical rehabilitation after injury, pain management, and in sports training EMS devices are available, e.g., from Compex Technologies, Inc. (New Brighton, Minn.) (now owned by DJO, Inc., Vista, Calif.), and such machines may be used to deliver a stimulus to at least one muscle of expiration in various embodiments of the invention.

In some embodiments, a stimulus is delivered to at least one abdominal muscle. Abdominal muscles of main interest in various embodiments of the instant invention are the rectus abdominis muscle, the external oblique, the internal oblique, and the transversus abdominis. The rectus abdominis muscle is a paired muscle running vertically on each side of the anterior wall of the human abdomen (and in some other animals). The external oblique muscle (also external abdominal oblique muscle) is the largest and the most superficial (outermost) of the three flat muscles of the lateral anterior abdomen. The internal oblique muscle is the intermediate muscle of the abdomen, lying just underneath the external oblique and just above (superficial to) the transverse abdominal muscle. The transversus abdominis muscle is a muscle layer of the anterior and lateral abdominal wall which is deep to (layered below) the internal oblique muscle. Nerves supplying one or more abdominal muscles include the inferior five intercostal, subcostal, and iliohypogastric nerves.

The number, shape, and position of the electrodes can vary and may be selected by one of skill in the art. For example, in some embodiments, between 2 and 16 electrodes may be used. In some embodiments, between 3 and 8 electrodes are used. The electrodes may be substantially square, rectangular, circular, or have other shapes. Exemplary lengths of the side(s) of a rectangular electrode may range, e.g., from about 4 cm-16 cm. In some embodiments, at least some of the electrodes are elongated strip-like shape (e.g., about 2-4 cm wide and about 12-20 cm long). The position of one or more of the stimulating electrodes may be selected so as to predominantly stimulate, e.g., the rectus abdominis muscle, or portion(s) thereof. In some embodiments, the rectus abdominus and external oblique muscles are stimulated. In some embodiments, electrodes are positioned on the abdomen under the costal margin and above the symphysis bone. Electrodes may be positioned approximately symmetrically around the midline. In some embodiments, a single electrode is positioned approximately on the mid-line, and one or more electrodes are approximately symmetrically placed on each side of the midline (e.g., one on each side). In some embodiments, an electrode or arrangement of electrodes may be approximately V-shaped and symmetrically positioned about the subject's midline with the apex pointing downwards. In some embodiments, or more pairs of elongated, strip-like electrodes may, for example, be placed so that they run diagonally downwards under costal margin on each side of the midline. In some embodiments, electrodes are positioned on the posterior thorax, so that they stimulate the nerve roots supplying muscles of expiration. It will be appreciated that a current may be delivered via one or more of the electrodes and returned via different electrode(s). Furthermore, not all of the electrodes may be "active"during any given breathing cycle. For example, it may be desirable to alternate between stimulating primarily two or more different muscles or groups of muscles in alternate breathing cycles or in successive breathing cycles during which a stimulus is delivered.

The characteristics of the electrical stimulus (also referred to herein as "stimulus parameters") can be selected by one of skill in the art to cause contraction of at least some expiratory muscle(s) without causing untoward effects such as unacceptable discomfort or heat. Characteristics of the stimulus that may be selected include, e.g., frequency, amplitude, duty cycle, pulse shape, pulse width, pulse duration, etc. In some embodiments, a stimulus delivered in synchrony with exhaling comprises a pulse train delivered at between 1 Hz and 200 Hz, with an amplitude of stimulation between 30 mA and 500 mA, and a pulse width between 10 µs and 100 µs, for a duration between 0.1 seconds and 2 seconds. In some embodiments, a voltage is between 0.1 V and 5 V. It will be understood that a variety of suitable combinations of parameters can be selected within the foregoing ranges or outside these ranges. In some embodiments a pulse width of between 100 µs and 1,000 µs may be used. In some embodiments, a voltage between 5 V and 300 V may be used. In some embodiments, a voltage between 50 and 200 V, e.g., about 100-150 V, may be used. In some embodiments, a voltage up to approximately 300 V and/or currents up to around 100 mA may be used with a stimulation period of about, e.g., 0.1 to 0.5 ms. In some embodiments, high voltage stimulation voltages up to 1000 V and/or currents up to over 1000 mA may be used, e.g., with a very brief stimulus duration. If the stimuli are delivered externally, stimulus parameters may be selected based at least in part on the different depth within the body to which the stimulus is to be delivered.

In some embodiments, a stimulus delivered in synchrony with an exhalation consists of a single pulse. In some embodiments, the amplitude of the pulse or pulses varies within the exhalation. For example, the pulse(s) may be triangular, square, rectangular, sinusoidal, partial sinusoidal, sawtooth, etc. In some embodiments in which multiple pulses are delivered within an exhalation period, the pulse width can vary. Variation of pulse magnitude and/or width can be linear. For example, a pulse train may begin at a 25 µs pulse width and increase in a linear manner to a pulse width of about 300-400 µs over a 1 second period of stimulation at, e.g., 50 Hz. Non-limiting examples of stimulus parameters are: (1) 1-second pulse train at 45 Hz, amplitude of stimulation 60-100 mA, and pulse width 25 µs; (2) single pulse, amplitude of stimulation between 50 mA and 450 mA, pulse width 200 µs. In some embodiments, the stimulus parameters are selected to cause gradual rather than abrupt contraction of the muscle(s), e.g., by using a varying (increasing) pulse width and/or amplitude within a stimulus period.

In some embodiments, stimuli having different characteristics may be delivered to different muscles using different electrodes. Furthermore, different stimuli may be delivered to different portions of a muscle. For example, stimulus parameters appropriate to stimulate and cause contraction of the upper portion of the abdominis rectus, lower portion of the abdominis rectus, transversus abdominis, and/or obliques may be selected, and corresponding stimulus may be delivered specifically to those regions (e.g., via overlying cutaneous electrodes). Electrode sizes and shapes may be selected from a variety of alternatives so as to optimize stimulation and cause contraction of particular muscle(s) or portions thereof and/or to avoid or minimize stimulation and contraction of other muscle(s) or portions thereof. (It is noted that "optimize", "optimal", and like terms as used herein do not require an absolute optimum or "best" among all possible alternatives but rather generally represent one or more preferred alternative(s) (e.g., for a particular purpose) among a variety of available alternatives. Such preferred alternative(s) may include the "best" alternative for a particular purpose.)

The timing of delivery of the stimulus within the expiratory phase of breathing can vary. In some embodiments, delivery of the stimulus is triggered by the end of inspiration. In some embodiments delivery of the stimulus is triggered by the onset of exhalation (e.g., by the beginning of a decrease in lung volume). A change in magnitude or slope or rate of change of slope of a quantity detected by a sensor (or a derived quantity such as tidal volume) can be used to detect, e.g., the onset of exhalation and/or the end of inspiration. In some embodiments, a peak detection or zero crossing detection algorithm may be used for one or more such purposes. As noted above, the delivery of the stimulus can start at a predetermined time after the end of inspiration or a predetermined time after the onset of exhalation. For example, delivery can begin between 0.5 sec and 2 sec after the onset of exhalation and last for an appropriate amount of time to cause contraction of muscles of exhalation but allow sufficient time for such muscles to at least in part cease contracting before inspiration begins. In some embodiments a stimulus lasts for between 1 and 1.5 seconds. In some embodiments, the stimulus delivery is timed so as to increase the force of contraction of expiratory muscles during the latter 0.5-1 seconds of exhalation. In some embodiments, a signal is provided to the stimulus device based on analyzing the subject's breathing, so as to terminate the stimulus in advance of or at the beginning of inspiration. Thus in some embodiments, at least two signals are provided to the stimulus device (within a respiratory cycle), wherein a first signal causes delivery of the stimulus and a second signal terminates delivery of the stimulus within that respiratory cycle. It will be understood that a second signal may be a change in one or more characteristics of a first signal. For example, a first signal may comprise a waveform. An alteration in the amplitude and/or frequency of the waveform may serve as a second signal. Different amplitudes and/or frequencies may encode multiple distinct instructions to the stimulus device.

A set of stimulus parameters or a sequence of different sets of stimulus parameters may be referred to as a "program" or "protocol". Different stimulus protocols may be selected, e.g., to increase force production, take account of different activity levels, and/or, in some embodiments of the invention, to increase muscle strength or endurance, enhance fatigue resistance, etc. In some embodiments, a protocol includes gradually changing at least some of the stimulus parameters over time. For example, the stimulus may begin at a low intensity or frequency during a given session and increase in intensity or frequency over, e.g., a predetermined time period (which may in some embodiments be selected by a user) or based at least in part on assessment of respiratory or other parameters of the subject by the apparatus itself.

As described herein, in some aspects, the invention relates to using feedback from a respiratory sensor to deliver a stimulus to the lower thorax and/or the abdomen of a subject when the subject is exhaling, e.g., so as to assist the subject with exhaling. In some embodiments of the invention, at least some stimulus parameter(s) may be adjusted dynamically (e.g., on a breath-to-breath basis or over an average of a number of breaths) based on input from one or more sensor(s). For example, the timing (e.g., relative to the end of inspiration or onset of exhalation), duration, intensity, frequency, and/or location of the stimulus can be adjusted. In some embodiments, such adjustment is based at least in part on the tidal volume inhaled prior to a particular exhalation during which the stimulus is delivered. In some embodiments, the apparatus analyzes the effect of a stimulus on the subject's breathing and adjusts the stimulus. The invention may thus employ feedback to adjust, e.g., optimize the stimulus parameters.

The stimulus can be generated, for example, using any of a wide variety of available stimulus generators or modifications thereof. In some embodiments a constant current stimulator is used. In some embodiments a constant voltage stimulator is used.

In some embodiments, a commercially available abdominal muscle stimulator is used, and/or stimulus parameters employed in such device are used; however in some embodiments, delivery of the stimulus is limited to the expiratory phase of breathing. The stimulus device may be an electrical abdominal muscle stimulator which, in some embodiments, is in the form of a belt (and may be referred to as an abdominal toning belt). Exemplary devices that may be used to stimulate one or more abdominal muscles are described, e.g., in U.S. Pat. Nos. 4,763,660; 6,341,237; U.S. Pub. Nos. 20040039426; PCT application publications WO/2000/041764; WO/2006/121463; WO/2006/113802; WO/2010/136486, and references therein. Abdominal muscle stimulators are commercially available, e.g., the devices known as "Flex Belt" or "Slendertone FlexGo Abdominal Toning System". A number of these devices have been cleared by the U.S. Food & Drug Administration (FDA) for muscle conditioning purposes. See, e.g., FDA 510(k) devices under Product Code ngx. Beurer GmbH (Ulm, Germany) offers abdominal muscle stimulation belts such as models EM30 and EM35 abdominal toning belts.

In some aspects, the inventive apparatus comprises a RIP sensor or piezoelectric respiratory sensor in signal communication with an abdominal muscle stimulator. In some embodiments, the sensor and abdominal muscle stimulator are directly connected via a conductive wire or cable. In some embodiments, the sensor and the abdominal muscle stimulator are both connected to a component that accepts an input signal from the sensor and delivers an output signal to the abdominal muscle stimulator, wherein the output signal causes the abdominal muscle stimulator to stimulate at least some abdominal muscles, e.g., at least the rectus abdominis. The component can comprise appropriate electronics to analyze the signal received from the sensor, determine when exhalation is occurring, select appropriate stimulus parameters, and/or deliver an appropriately timed signal to the abdominal muscle stimulator so that the abdominal muscle stimulator will stimulate the abdominal muscles during exhalation.

In some embodiments magnetic stimulation of the expiratory muscles is used, optionally together with electrical stimulation. For example, the spinal nerve roots around the level of T8-T12 may be activated, e.g., by delivering stimulation, e.g., magnetic stimulation over the T10 spinous process. A stimulus may also or alternately be delived to other locations on the posterior thorax in certain embodiments of the invention.

In some embodiments of the invention, the device is at least in part implanted, e.g., into the subject's thorax or abdomen, and the electric and/or magnetic impulses are delivered internally, e.g., to efferent nerve(s) supplying expiratory muscles and/or to the muscles themselves.

In some embodiments, a subject's breathing pattern is analyzed (e.g., using a spirometer) and/or one or more physical or neurolomuscular characteristics such as chest and/or abdominal dimension(s), expiratory and/or inspiratory muscle strength, sensitivity of efferent and/or afferent nerve(s) supplying said muscle(s) is/are assessed, e.g., prior to using the apparatus. The analysis may be used, e.g., to calibrate or select the sensor(s) and/or stimulus device based at least in part on the subject's individual breathing pattern and/or physical characteristics. Appropriate parameters or ranges of parameters for the stimulus, electrode number and/or position, etc., may be selected (either automatically by the apparatus itself or by a health care provider or other appropriately trained individual) to provide effective and well tolerated stimulation. For example, the minimum electrical stimulus required to reliably elicit effective contraction of one or more expiratory muscle(s) (e.g., the rectus abdominis) or to achieve a desired level of reduction in EELV and/or the maximum stimulus that may be delivered without causing undue discomfort may be determined. In some embodiments stimulus parameters that are the minimum required (e.g., minimum current required) to produce observable contraction (e.g., observable to the naked eye) of a selected muscle or muscles of a particular subject are used. In some embodiments stimulus parameters at the maximum level (e.g., maximum current) that the subject can reasonably tolerate are used. In some embodiments stimulus parameters between the afore-mentioned minimum and maximum are used. Thus in some aspects, the invention provides breathing assistance apparatus that is customizable based on a subject's individual characteristics.

In some embodiments the apparatus is capable of detecting different breathing patterns, e.g., breathing patterns associated with cough, quiet breathing, breathing patterns associated with speaking, etc. In some embodiments, the apparatus adjusts one or more stimulation parameters and/or signal conditioning procedures based at least in part on detection of different breathing patterns. For example, stimulus intensity and/or duration may be altered based at least in part on the breathing pattern. In some embodiments stimulation is stopped during certain breathing types, e.g., breathing types associated with speaking, and, in at least some embodiments, stimulation is restarted automatically after a subject stops speaking. In some embodiments, detection of different breathing patterns is performed using a statistical classifier such as a maximum likelihood classifier or a Bayesian classifier. In some embodiments, detection of different breathing patterns is performed using thresholds, e.g., using the minimum amplitude of the sensor signal during inhalation to distinguish between cough and quiet breathing. In some embodiments, a set of breathing pattern "training examples" of different breathing types is acquired for a particular subject and used to generate a model or reference pattern that can be used to subsequently assign breathing patterns into one category or another. In some embodiments a model or reference pattern is generated for a subject in various positions, e.g., lying down, sitting, standing, walking. In some embodiments an algorithm based on a cross-correlation analysis of a subject's breathing pattern with one or more reference patterns for various breathing types in that subject may be used. See Gollee, H., et al., Med Eng Phys. 29(7):799-807 (2007) and/or Gollee, H. et al., Technol Health Care. 16(4):273-81 (2008) for an example of detecting and distinguishing breathing patterns associated with cough and quiet breathing using cross-correlation. Any of various machine learning approaches known in the art may be used in various embodiments. In some embodiments an apparatus comprises or interfaces with an accessory sensor or device that detects subject movement that is not part of the breathing cycle, such as walking or volutary movements during sleep such as turning over. Such sensor or device may comprise an accelerometer or may comprise an electrode placed on an arm or leg, for example. In some embodiments input from an accessory sensor or device is used to determine the nature or intensity of the subject's physical activity, and, in some embodiments, such information is used to adjust one or more stimulus parameters or signal conditioning parameters. For example, in some embodiments information regarding a subject's movement is used to determine whether input from a breathing sensor contains an artifact arising from movement that is not part of the breathing cycle.

It is also within the scope of the invention to deliver a blocking stimulus that blocks contraction of one or more muscle(s) and/or blocks conduction by one or more nerve(s). For example, it may be desirable to block sensory impulses during at least part of a respiratory cycle. The time period within a respiratory cycle during which the blocking stimulus is delivered may or may not overlap with the time period in which the stimulus that elicits contraction is delivered. In some embodiments, contraction of at least some of the lower external intercostal muscles (located in intercostal spaces 7 and below) is blocked while contraction of at least some of the lower internal intercostal muscles (located in intercostal spaces 7 and below) is stimulated. Appropriate parameters for blocking rather than eliciting contraction may be selected. Different sets of electrodes may be used for the different stimuli.

One, two, or more pulse generators and/or current or voltage sources may be provided, e.g., to permit convenient delivery of multiple stimuli.

In some embodiments of the invention, at least some muscles of inspiration are stimulated (electrically or magnetically) while a subject is inhaling. In other embodiments, such stimulus is not provided (or any such stimulus is insufficient to cause contraction or significant change in force generated by such muscles). For example, the diaphragm is not stimulated and/or the external intercostal muscles are not stimulated (or any such stimulus is insufficient to cause contraction or significant change in force generated by such muscles). In at least some embodiments of the invention, a stimulus is not delivered to the central nervous system. In at least some embodiments of the invention, a stimulus is not delivered to the phrenic nerve.

Electrodes

A variety of electrodes and electrode attachment means can be used in the apparatus of the invention, e.g., for sensing and/or for delivery of an electric stimulus. For example, electrodes may be contained in pads that adhere to the skin. Electrodes may be disposable (intended for only one to several uses) or may be intended for medium term use (e.g., between 1 week and 6 months) or long term use (e.g., 6 months or more). Electrodes suitable for contacting the human body externally (on the skin) or internally are known in the art. An electrode may be a "wet" electrode that requires use of a contact gel when used on the skin or a "dry" electrode that does not require a contact gel. In some embodiments, an electrode is made at least in part of a conducting carbon material. In some embodiments, a conducting polymer is used. For example, a conducting polymer based on 3,4-ethylenedioxythiophene such as PEDOT (poly (3,4-ethylenedioxythiophene)) or a PEDOT:PSS (poly(3,4-ethylenedioxythiophene)) poly(styrenesulfonate) composite may be used to fabricate a dry electrode. An electrode suitable for placement on the skin can be incorporated into an adhesive patch or pad or attached to a garment (e.g., by sewing, snap or button fasteners, Velcro, or other fastening means). Electrodes can be independently positionable. In some embodiments, electrodes are connected to one another or provided as an electrode array, e.g., arranged in a predetermined pattern with respect to one another.

Axelgard Manufacturing Co., Ltd. (Falbrook, Calif.) and PCP Medical, Inc. (Batavia, N.Y.) supply a range of different electrodes that may be used in various embodiments of the invention. For example, PALS®, UltraStim®, or Valu-Trode® electrodes (Axelrod Manufacturing Co., Ltd.) may be used in various embodiments of the invention.

Mechanical Stimulus Device

A device that delivers a mechanical stimulus to the lower anterior thorax and/or abdomen may be implemented in a variety of ways. The mechanical stimulus typically delivers sufficient force to the subject's lower anterior thorax and/or abdomen to cause an increase in intrathoracic pressure, which assists in exhalation. For example, the external compression may be sufficient to push the abdominal contents up, facilitating expiration. As the external compression is relaxed, abdominal contents return to their uncompressed position, e.g., by means of gravity and/or elastic recoil, permitting inspiration to occur.

In some embodiments, a mechanical stimulus device comprises an electroactive polymer (EAP). Electroactive polymers are polymers that exhibit a change in size or shape when stimulated by an electric field. Examples of such polymers are described, e.g., in U.S. Pat. Nos. 6,249,076; 6,545,384; and 6,376,971. See also U.S. Pat. No. 7,491,185 for discussion. EAPs can comprise conductive polymers, ionic polymer-metal composites (IPMCs), or responsive gels. Polyaniline, polypyrrole, polysulfone, and polyacetylene are exemplary EAPs whose use is contemplated (optionally combinations thereof may be used). EAPs may be in the form of fibers, which can be woven directly into a garment or belt. The fibers may be interspersed in a garment or belt such that they extend circumferentially around the subject's lower anterior thorax and/or abdomen in one or more substantially horizontal strips or rows, which may be separated by regions that do not comprise the EAP.

In some embodiments, a mechanical stimulus comprises pneumatically driven compression. For example, the device can comprise one or more compartment(s) or bladder(s) into which a gas (e.g., air) can be introduced or released. One or more compartment(s) is/are positioned such that expansion of the compartment(s) by introduction of a gas compresses the anterior thorax and/or lower abdomen. In some embodiments, a gas is moved back and forth between two compartments. During exhalation, gas is introduced into a compartment positioned above the lower anterior thorax and/or abdomen, thereby compressing these regions. The gas is released (e.g., into the other compartment) prior to or shortly after the onset of inhalation. The compartment(s) may be secured to the subject's body using a harness, yoke, or corset assembly or the like. Use of pneumatic artificial muscles that at least in part encircle a subject's lower thorax and/or abdomen are also envisioned. Compressed gas or a compressor may be provided.

In other embodiments, mechanical force is provided by motorized belts positioned around the subject's chest and/or abdomen that tighten during exhalation and then loosen.

Parameters for the mechanical stimulus may be selected to provide a steady or gradually increasing compressive force and may avoid delivering a sudden impact to the thorax or abdomen or an unduly rapid and potentially uncomfortable change in compressive force experienced by the subject. The mechanical stimulus may last, for example, for between about 0.5 and 3 seconds in various embodiments.

Power Supply

The apparatus of the invention can comprise a power supply that supplies electric energy to the stimulus generator. Energy may be obtained from a suitable energy source such as an electrical energy transmission system supplying AC voltage or energy storage device such as one or more batteries. A power supply may be implemented as a discrete, stand-alone device or as an integral component of the device. A power supply can comprise one or more batteries, which can be provided as a battery pack. The batteries can be rechargeable. The apparatus can comprise a power cord that can be plugged into a standard electrical outlet, e.g., for use while the subject is not ambulating or remains close to the outlet and/to permit recharging the batteries. In some embodiments, a battery pack (or power supply) is separable from the remainder of the apparatus to permit conveniently charge one battery or set of batteries while using the other(s). A power supply can comprise a safety feature such as a current or voltage limiting circuit.

Controller

In some aspects, the apparatus comprises a controller that serves as a link between one or more sensor(s) and a stimulus device. The controller may comprise a processor (e.g., a microprocessor), memory (e.g., both ROM and RAM), means for accepting one or more input(s) (e.g., from one or more sensor(s)), and means for providing one or more output(s) (e.g., to stimulus device). In some embodiments, a microcontroller is used, in which the afore-mentioned functions are provided by a chip comprising a single integrated circuit and multiple pins for input/output. The controller may analyze signal(s) received from one or more sensor(s) and determine whether and when to provide an output to a stimulus device. For example, the controller receives signal(s) from one or more sensor(s), analyzes the signal(s), and outputs a signal to a stimulator in response to said signal(s). The stimulator then delivers a stimulus to the subject in response to the signal from the controller. Optionally, the controller selects stimulus parameters based at least in part on analysis of the signal(s) received from the sensor(s). The analysis may consider signal(s) received during multiple breathing cycles. For example, if the breathing rate is increasing over time or exceeds a predetermined value, or if the duration of exhalation is decreasing over time, the controller may change one or more parameters of the delivered stimulus to increase so as to result in more intense muscle contraction. In some embodiments a controller may alter one or more stimulation parameters for a given breath type, e.g., quiet breathing, based on sensor feedback, e.g., to account for minor variations. For example, in some embodiments increasing intensity of stimulation is provided if the amplitude of a breath signal decreases over time, e.g., over at least a specified number of breath cycles.

It will be appreciated that signal processing and analysis functionality may be provided at least in part by the sensor(s) themselves and/or by the stimulus device. For example, a sensor can comprise an analog to digital converter and/or be designed to provide a signal to the controller (or to the stimulus device) only when the physical quantity measured by the sensor exceeds a predetermined value.

Computer-readable instructions stored on a computer-readable medium for carrying out at least part of the signal analysis, stimulus parameter selection functions, and/or other function(s) of the apparatus are an aspect of the invention. Computer-readable instructions may be embodied in any tangible medium (e.g., a non-transitory storage medium) and/or may utilize any computer programming language in various embodiments. A computer-readable medium may be, for example but not limited to, an electronic, magnetic, optical, electromagnetic, infrared, or semiconductor system, apparatus, device. Examples of a computer-readable medium include the following:, a hard disk, a random access memory (RAM), a read-only memory (ROM), an erasable programmable read-only memory (e.g., EPROM or Flash memory), a portable compact disc read-only memory (CDROM), a floppy disk, an optical storage device, or a magnetic storage device. A computer-readable medium may in some embodiments be paper or another suitable medium on which the program is printed or embodied, as the program can be electronically captured, for instance, via optical scanning of the paper or other medium (optionally employing optical character recognition), then compiled, interpreted, or otherwise processed in a suitable manner, if necessary, and then stored in a computer memory and/or executed by a computer processor. In the context of this document, a computer-readable medium may be any medium that can contain, store, communicate, propagate, or transport data or computer-executable instructions.

Garment or Belt

In some embodiments, at least one component of the inventive apparatus is integrated into a garment, by which is meant that the component is attached to the garment as an integral part of the garment. For example, the sensor, electrode(s), stimulus device, and/or electrical cords connecting two or more component(s) are integrated into a garment. In some embodiments, the sensor, stimulus device, or both (or one or more component(s) thereof) are attached to a garment but are readily detachable, e.g., they are attached by a fastening means selected to permit easy detachment.

A garment may be an upper body garment that a subject can pull over the head and thorax. It is typically a close-fitting garment that may fit snugly around the thorax and, in some embodiments, extends to and fits around at least part of the abdomen (e.g., the upper abdomen). In one aspect, the invention provides a comfortable and unobtrusive garment having at least one sensor integrated therein, wherein the sensor is operably connected to a device adapted to deliver a stimulus to a subject, wherein the stimulus is effective to assist the subject with breathing. The garment may be an undergarment suitable for wearing under a conventional shirt or blouse (if desired). For example, the garment may be a vest or "T-shirt". In some embodiments, the garment is sleeveless while in other embodiments sleeves (either short or long sleeves) are provided. In other embodiments, at least the device for delivering the stimulus may be incorporated into a lower body garment that a subject pulls on over the legs, e.g., an undergarment such as a pair of briefs or a girdle, or a pair of shorts, tights, pants, leggings, etc. The lower body garment fits at least around the subject's abdomen and, optionally, at least part of the lower thorax. In some embodiments the garment is a bodysuit or leotard-like garment.

In some embodiments, the sensor, stimulus delivery device, or both, are integrated into a belt that is worn around the waist (i.e., the part of the abdomen between the rib cage and hips). The belt may be wider than a conventional belt used as a clothing accessory and may in some embodiments encompass at least a portion of the lower rib cage and/or extend down over at least part of the hip region. The belt is typically comprised of a flexible material such that it can encircle the subject's waist. It will typically have a fastening means such as one or more buckles, hooks, snaps, buttons, or Velcro fasteners. The belt may be flexibly adjustable about the abdomen.

The sensor and the stimulus device may be integrated into the same garment or belt, or each may be integrated into a different garment or belt. In some embodiments, the stimulus device is integrated into a belt wearable around the subject's waist while the sensor device is integrated into an upper body garment. The sensor and device may communicate via a direct electrical connection or wirelessly. In some embodiments, a belt or garment comprises multiple sites for potential attachement of electrodes, thereby permitting an individual (e.g., the subject or a health care provider or other caregiver) to adjust the number and/or position(s) of the electrodes (for sensing and/or stimulus delivery).

The garment or belt may be made at least in part of a stretchable material comprising fibers with high elasticity such as Spandex (also called Lycra or elastane), Darlexx, or polyurethane, to facilitate snug fitting, which fibers may be intermixed with other fibers such as cotton or polyester. The garment or belt may be composed at least in part of a woven, non-woven, or meshlike fabric or textile. In some embodiments, a garment or belt is comprised at least in part of an elastomeric material such as a synthetic rubber material, e.g., polychloroprene (Neoprene). The garment or belt may have a Spandex or nylon-containing backing lining at least on one side for contacting the skin, e.g., to improve comfort. In some embodiments, the garment or belt comprises multiple panels or sections, wherein at least some of the panels or sections comprise a stretchable material. The garment or belt may comprise padding or cushions or the like or may in part be composed of a soft and cushiony material that may serve to protect sensitive component(s) and/or improve the comfort of the subject.

Conductive strips may be woven into or attached to the garment or belt, e.g., as sensors and/or to transmit signals from sensor(s) and/or to or from a stimulus device. Components such as a sensor or electrode(s) may be attached to the garment or belt by, e.g., sewing, embroidering, embedding, adhering (e.g., using a suitable adhesive that, in some embodiments, is pressure-sensitive), weaving, enclosing at least part of the component between portions or layers of fabric, lacing, use of tabs, slots, or grooves, tapes, zippers, etc. In some embodiments, a sensor and/or electrode is printed or stamped onto a fabric. The garment or belt may be washable. In some embodiments, the garment or belt is designed so that sensor(s) and/or electrode(s) for delivering a stimulus can be positioned at a variety of different locations. For example, the garment or belt may comprise multiple snap fastener disks or press stud disks that would permit attachment of a sensor or electrode thereto.

As noted above, electroconductive or piezoelectric fibers can be used as sensors in various embodiments of the invention. Such fibers may optionally be an integral part of a garment or belt. For example, the garment or belt may comprise one or more regions, optionally in the form of strips or bands, that comprise conductive or piezoelectric fibers or fabric portions. Such regions may optionally extend around the subject's chest or abdomen. They may be substantially straight or arranged in a zig-zag, sinusoidal, or similar-shaped pattern.

A garment or belt may contain one or more "channels" or "tunnels" comprised of two or more fabric layers through which one or more electric cords or cables can be "threaded" to connect various components of the apparatus. A garment or belt may comprise one or more "pockets" or spaces between two or more fabric layers into which one or more components of the apparatus may be placed. For example, a power supply, controller, compression compartment, electric impulse generator, etc., may be placed in a pocket or between fabric layers. Pockets may be connected by channels or tunnels within the garment or belt.

In particular embodiments, the invention provides a wearable abdominal muscle stimulating belt comprising a sensor capable of sensing when a subject is exhaling. In some embodiments, the belt comprises two or more sensor(s). The sensors may be positioned so that a first sensor contacts the right upper quadrant of the anterior abdomen and a second sensor contact the left upper quadrant of the anterior abdomen. The sensor(s) may detect strain and/or abdominal movement that accompanies breathing activity. The sensor(s) may be positioned on the belt in a preferred orientation for sensitivity and/or specificity of sensing when a subject is exhaling. In some embodiments, the sensor(s) are piezoelectric sensors.

It is particularly contemplated to attach or incorporate any one or more sensor(s) or sensor types mentioned herein or other suitable sensor(s) into an abdominal muscle stimulating belt. It is also particularly contemplated to provide an abdominal muscle stimulating belt comprising means for attaching attach or incorporating any one or more such sensor(s). It is also particularly contemplated to use the abdominal muscle stimulating belt with sensor(s) to stimulate at least one abdominal muscle in phase with a subject's exhalation. It is particularly contemplated to provide an apparatus comprising an abdominal muscle stimulating belt with sensor(s) and control means to process signal(s) from the one or more sensor(s) and cause the delivery of an electrical stimulus to one or more abdominal muscle(s) when a subject is exhaling.

In some embodiments, the belt is equipped with means that permit attachment of one or more sensor(s) thereto, such that the sensors contact the subject in a manner appropriate to permit the sensor(s) to detect when a subject is exhaling. In some embodiments, the belt comprises one or more loops (similar to belt loops found on garments such as trousers), wherein the loops are located on the surface of the belt that would contact the subject's skin when the belt is in use. In some embodiments, the sensor(s) are in the form of bands or strips that can be attached to the belt by sliding them through the loops of the belt. In some embodiments a sensor comprises a tab (e.g., a short strip of material attached to or projecting from a side of the sensor), which can fit into a slot or slit in the belt. The tab may be made at least in part of a reasonably stiff material, e.g., a plastic material. The inner surface of the belt may alternately comprise, or further comprise, one or more hooks, loops, eyes, snaps, slots, slits, grooves, or other means or features that would permit secure fastening of the sensors. Thus the invention encompasses use of attachment systems wherein a stimulus device, e.g., an abdominal muscle stimulating belt, comprises a first element of the attachment system and a sensor comprises a second element of the attachment system, wherein the first and second elements are compatible with each other so that the sensor may be securely attached to the belt. Example of such attachment systems and the respective elements include, e.g., "male"and "female" portions of a snap; tab and slit/slot; hook and loop; hook and hook; hook and eye; button and button hole. (It is noted that hook and loop, is intended to encompass use of miniature hooks, loops, and/or eyes, e.g., as in Velcro). One or more such attachment systems may be used. A first element may be provided by the belt and a second element provided by the sensor, or vice versa.

In some embodiments, the sensor(s) constitute an integral part of the belt. For example, one or more sensor(s) may be sewn or securely adhered to the side of the belt that would contact the subject when in use.

The locations of the integral sensor(s), attachment element(s), and/or electrodes may be selected so that the sensing element(s) do not spatially overlap with the electrodes. In some embodiments, sensing elements and electrodes are spaced apart along the inner side of the belt or garment.

Kits

The components of the inventive apparatus can be provided separately or together e.g., within a single package or "kit", within which they may be individually wrapped or otherwise separated. The kit or package would contain at least a sensor (and optionally associated elements such as bands to secure the sensor)and a stimulus device (e.g., an abdominal muscle stimulator), and optionally further include one or more of the following: electrode(s), electrode gel, controller, power supply, wires for connecting component(s), instructions for use of the apparatus, etc. In some embodiments, a kit or package comprises an abdominal muscle stimulator (e.g., in the form of a belt) and a RIP sensor or piezoelectric sensor suitable for sensing breathing. In some embodiments, the sensor is incorporated into a garment or belt. Optionally the kit or package contains a notice (e.g., label or package insert) indicating that the apparatus has been cleared or certified by a regulatory authority such as the FDA, e.g., for over the counter and/or prescription use. In some embodiments one or more indications for which the apparatus is approved is mentioned in the notice. For example, in some embodiments a notice indicates that the apparatus is approved for use to assist breathing, reduce hyperinflation, and/or improve exercise tolerance in a subject suffering from obstructive respiratory disease, e.g., COPD. In some embodiments a notice indicates that the apparatus is approved for use in assisting with ventilator weaning.

Features and Uses

Without limiting the invention in any way, this section provides further information relating at least in part to various features and uses of embodiments of the inventive apparatus and methods. In some aspects, an inventive apparatus is used to treat a subject. A subject is typically a human although it is envisioned that a subject may, for therapeutic and/or testing purposes, be a non-human animal, e.g., a non-human primate or domesticated animal, e.g., companion animal such as a dog or cat. In some embodiments the subject is male. In some embodiments the subject is female. In some embodiments the subject is an adult, e.g., a human at least 18 years of age, e.g., between 18 and 100 years of age. Many subjects with COPD may be adults over the age of 40. An effective treatment in some embodiments of the invention reduces the severity of one or more symptoms, signs, or manifestations of a disease, disorder or condition during at least part of the time that the treatment is being used by the subject.

A subject suffering from a respiratory disorder, e.g., an obstructive respiratory disorder such as COPD, can be diagnosed as known in the art. See, e.g., the GOLD Report. The increase in airway resistance is evident by a decrease in the forced expiratory volume in 1 second ($FEV_1$), e.g., as measured by spirometry or a peak flow meter. COPD may be defined as a forced expiratory volume in 1 second to forced vital capacity ratio ($FEV_1/FVC$) that is less than 0.7. In some embodiments, a subject has COPD of Stage II, III, or IV as defined in the GOLD Report based on post-bronchodilator assessment of $FEV_1/FVC$ and $FEV_1$. For example, a subject may have $FEV_1/FVC<0.70$ and $30\% \leq FEV1<50\%$ of predicted value (e.g., <50% of value predicted for a healthy individual based on individuals's age, sex, and height) or $FEV_1/FVC<0.70$ and $FEV_1<30\%$ of predicted. In some embodiments, a subject has symptoms of COPD not fully reversible with bronchodilator therapy and an $FEV_1/FVC$ in the lower 5% of healthy individuals in the subject's age group. Other spirometry-based definitions of airway obstruction (e.g., British Thoracic Society definition) could be used. In some embodiments a subject exhibits EFL as assessed, e.g., using the NEP technique. For example, in some embodiments a subject has a score of 1 or 2 using a 3 point scale, or a score of 0 to 4 using 5 point scale, or EFL less than 50% expiration using the continuous scale.

In some aspects, use of an inventive breathing assistance apparatus reduces the objective or subjective effort required for the subject (e.g., a subject with an obstructive respiratory condition, e.g., COPD) to at exhale and/or inhale, e.g., if the subject feels that it is generally easier to exhale and/or inhale when using the apparatus than when not using the apparatus (at the same activity level). As noted above, it should be understood that any one or more benefits provided by the inventive apparatus may not be evident immediately upon the subject beginning a session of using the apparatus. For example, some time may be required for the stimulus provided by the apparatus to result in exhalation of air trapped in the subject's lungs. For example, the EELV may gradually decrease over a period of time after the beginning of a session. In some embodiments, one or more beneficial effects provided by an inventive apparatus may be present for at least some time after the end of a session. For example, an effect may be evident for at least 15 minutes after a session, e.g., between 15 and 30 minutes, or up to 1, 2, 4, 6, or more hours after the end of a session. It will be appreciated that the effect may diminish over time during such period. Thus a beneficial effect is considered to result if the subject experiences the effect during at least part of a session and/or if the subject experiences the effect after completion of the session.

In some embodiments, use of an inventive breathing assistance apparatus results in a decrease of between 5%-75%, between 5% and 50%, or between 5% and 25% in the subject's resting EELV (e.g., as compared with the subject's resting EELV before the first use of the device by the subject). In some embodiments, use of an inventive breathing assistance system results in a decrease of between 50 ml and 200 ml in the subject's resting EELV (e.g., as compared with the subject's resting EELV before the first use of the device by the subject). In embodiments, use of an inventive apparatus results in a decrease of between 5%-75% and/or a decrease of between 50 ml and 200 ml in the subject's EELV during or immediately after a period of exercise, e.g., walking (e.g., as compared with the subject's EELV after such exercise before the first use of the device by the subject). In some embodiments, an inventive apparatus used by a subject experiencing dynamic hyperinflation (e.g., due to a COPD exacerbation) results in a decrease in the subject's EELV such that it is within 125% of that measured for the subject when not experiencing dynamic hyperinflation or a COPD exacerbation. In some embodiments, use of an inventive apparatus results in a decrease in a subject's EELV so that it does not exceed 150% or, in some embodiments, so that it does not exceed 125% of the average predicted EELV for healthy, matched subjects. As noted above, a change in EELV may exist during part of a session using the device and/or may continue for a period of time after a session is over. A "matched subject" will typically be reasonably matched with regard to age, height (and/or other relevant dimension(s)), optionally sex-matched. One of skill in the art will be aware of or can obtain suitable standard ranges for normal EELV (or other lung volumes, lung capacities, or characteristics relevant to breathing) in subjects. Assessment of EELV (or other lung volumes, lung capacities, or characteristics relevant to breathing) can be performed using any of the methods mentioned herein or others known in the art. Such measurement may be averaged over multiple breaths.

Using an apparatus of the invention that stimulates the abdominal muscle(s) may train these muscle(s) and may, for example, result in an increased strength and/or endurance. Thus the apparatus may improve a subject's own ability to exhale independent of the direct effect of the stimulus itself. It is also contemplated that the experience of using the apparatus may help train a subject how to use their abdominal muscles more effectively in exhaling. For example, the inventive apparatus may help the subject become aware of the capacities of their abdominal muscles and/or may help the subject gain increased control over their contraction and/or its timing. Using an inventive apparatus may teach a subject when to contract the abdominal muscles in order to better exhale. For example, an apparatus may assist the subject with appropriate timing of contraction with respect to the onset of exhalation and/or appropriate duration of contraction in order to facilitate one or more outcomes or goals such as, e.g., to exhale a selected volume, to retain no more than a selected volume in the lungs at end-expiration, to have a selected respiratory rate or a respiratory rate within a selected range, or to make efficient use of respiratory muscle effort.

In some embodiments, the inventive apparatus may be used as a tool in biofeedback. Biofeedback generally refers to a process that enables an individual to learn how to change physiological activity, e.g., for the purposes of improving health and/or performance and can involve becoming aware of various physiological functions using instruments that provide information on the activity of those same systems, with a goal of being able to manipulate them at will. This type of learning may occur naturally through use of the inventive apparatus, may be facilitated by a trained biofeedback practitioner, and/or may be facilitated by a computer-based program. The computer program may communicate with the apparatus and, for example, display waveforms associated with breathing, the time of delivery of a stimulus and/or its location or strength, comparison of breathing with and without the stimulus. Information can be presented to the user on a display. Visual and/or auditory feedback and/or tactile feedback (e.g., electrical or mechanical) may be provided to the subject. The computer program may be written in a suitable computer language and may be stored on computer-readable medium; such computer-readable medium is an aspect of the invention. The invention provides a system comprising an apparatus of the invention and a computer, wherein the computer is programmed to execute instructions for providing biofeedback to a user based at least in part on input received from the apparatus and/or while a subject is using the device.

In some embodiments an apparatus is capable of operating in at least two different modes, e.g., (i) a first mode in which stimulus parameters selected to stimulate contraction of one or more expiratory muscles are used during those breath cycles in which a stimulus is delivered, and (ii) a second mode in which stimuli below the level of stimulation that would be required to stimulate contraction of the expiratory muscle(s), under ordinary conditions of use (or in some embodiments, any effect on contraction would be insignificant in terms of its effect on exhalation, as judged by one of ordinary skill in the art) but sufficient to be felt by the subject, are delivered during at least some breath cycles. A stimulus as described in clause (ii) of the preceding sentence may be referred to herein as a "tactile stimulus", and the second mode may be referred to as a "prompting mode". In general, a tactile stimulus is sufficient to elicit an action potential in at least one sensory nerve, e.g., a sensory nerve supplying the skin, but in at least some embodiments, is not sufficient to elicit an action potential in a motor nerve supplying an expiratory muscle. In some embodiments a tactile stimulus is delivered at a frequency at or below about 15 Hz. In some embodiments, when operating in the second mode, tactile stimuli are delivered during at least 50%, 60%, 70%, 80%, 90%, 95%, or 100% of breath cycles in which a stimulus is delivered. In some embodiments stimulus parameters for a tactile stimulus are selected such that the stimulus does not, under ordinary conditions of use, elicit detectable expiratory muscle contraction of muscles that are not contracting (except as a result prompting the subject through sensory stimulation as described herein, e.g., below) and/or does not elicit detectable increase in the force or duration of contraction of muscles that are contracting (except as a result prompting the subject through sensory stimulation as described herein, e.g., below). In some embodiments, a "detectable effect" is visually observable to the naked eye. In some embodiments, a "detectable effect" is detectable by an appropriate sensor. In some embodiments, a "detectable effect" is detectable by electromyography (EMG). In some embodiments EMG is surface EMG. In some embodiments EMG is intramuscular EMG. In some embodiments parameters for a tactile stimulus are determined empirically for a subject. For example, in some embodiments stimuli at the minimum level required in order to be felt by the subject at least 80%, 90%, 95%, or more of attempts are selected.

In some embodiments, when in a prompting mode, sensory stimuli, e.g., tactile stimuli, are provided to serve as a cue for the subject with regard to the timing of respiration and/or respiratory muscle contraction. For example, in some embodiments a sensory stimulus, e.g., a tactile stimulus, provides a cue as to the appropriate beginning, duration, or end or one or more phases of respiration or expiratory muscle contraction in order for the subject to achieve a specified target with regard to, e.g., the volume exhaled or the duration of exhalation. In some embodiments a sensory stimulus serves as a cue to prompt the subject to initiate and/or maintain exhalation and/or to initiate or maintain or increase expiratory muscle contraction. For example, a subject may be instructed to continue to breathe out and/or to continue contracting the expiratory muscles for so long as he or she continues to feel the stimulus. In some embodiments a target is that the subject exhales for at least a specified period of time and/or exhales at least a specified volume. In some embodiments a target is at least in part predetermined prior to the beginning of a particular training session. For example, in some embodiments a target is that the subject exhales for at least a selected minimum time. In some embodiments a minimum time may be calculated on an individual basis as a percentage increase of a subject's pre-existing exhalation time when not using the apparatus. In some embodiments a target is selected based at least in part on a subject's recent breathing activity, as detected by the apparatus. For example, if the subject's exhalation phase and/or exhaled volume has decreased in length over each of at least a specified number of consecutive breathing cycles (e.g., at least 3 breathing cycles), the apparatus may prompt the subject to increase the duration of the next exhalation.

A prompting mode can be used for any of a variety of purposes in various embodiments. For example, in some embodiments a prompting mode is used to help a subject, e.g., a subject with an obstructive respiratory disorder, acquire a more effective breathing pattern. In some embodiments a prompting mode is used as an exercise aid. In some embodiments an apparatus is capable of operating in a mode in which a sensory stimulus is delivered during some respiratory cycles, and a stimulus of sufficient strength to elicit enhanced expiratory muscle contraction is delivered during at least some of the other respiratory cycles. In some embodiments the apparatus determines whether the subject met a target and, in some embodiments, selects a course of action based at least in part on whether the subject met the target. In some embodiments the apparatus determines whether the subject's breathing is trending in an unfavorable direction and, in some embodiments, selects a course of action based at least in part on whether the subject's breathing is trending in an unfavorable direction. A course of action may be, e.g., delivering a stimulus sufficient to elicit increased expiratory muscle contraction during the next exhalation if the subject failed to meet the target and/or if the subject's breathing is trending in an unfavorable direction or delivering a sensory stimulus (or no stimulus) if the subject met the target. For example, a stimulus that elicits increased expiratory muscle contraction may be delivered if the subject fails to meet a target or if the subject's breathing is trending in an unfavorable direction. In some embodiments an unfavorable direction is a direction indicating that the length of the subject's expiratory phase is decreasing. In some embodiments an unfavorable direction is a direction suggesting that the subject is developing hyperinflation or that hyperinflation is worsening. Any reasonable time period may be selected for purposes of determining whether the subject's breathing is exhibiting a trend in various embodiments. For example, in some embodiments a trend is detected by analyzing a subject's breathing over between 5 and 100 breaths or over between 30 seconds and 5 minutes.

In some embodiments a sensory stimulus comprises an electrical stimulus. The strength, nature, and/or other characteristics of the sensory stimulus may be selected by and/or customized appropriately for the particular subject. For example, an electrical stimulus that does not elicit enhanced expiratory muscle contraction but is reliably perceived by the subject may be selected based empirically. In some embodiments a sensory stimulus is provided using any one or more electrodes. In some embodiments an electrode delivers either a tactile stimulus or a stimulus sufficient to stimulate contraction depending, e.g., on the mode in which the apparatus is operating. In some embodiments one or more electrodes is provided solely for purposes of delivering a tactile stimulus. In some embodiments a sensory stimulus comprises an auditory stimulus or a visual stimulus. For example, in some embodiments an apparatus comprises or interfaces with a unit capable of producing one or more sounds or equipped with one or more lights (e.g., light emitting diodes), etc., which serve as a sensory stimulus. In some embodiments an apparatus provides information regarding the extent to which the subject achieved the target for a particular respiratory cycle, time interval, or session.

In some embodiments an apparatus may be capable of operating in a manner in which it stimulates one or more abdominal muscles to contract in synchrony with inspiration during at least part of the inhalatory phase. In this case, the abdominal muscles would work against the action of the diaphragm. Without wishing to be bound by any theory, it is envisioned that causing the abdominal muscles to work against resistance in this manner may be more efficient, e.g., may lead to greater or more rapid improvements in strength as compared with stimulation at random times relative to the timing of the respiratory cycle or relative to stimulation during exhalation. In some embodiments this type of functionality may be provided as one of multiple modes of an apparatus for use by individuals with compromised respiratory function who are in need of assistance with breathing. In some embodiments this type of functionality may be provided for use for abdominal muscle toning or strengthening purposes, e.g., by individuals who are not in need of assistance with breathing, e.g., individuals with normal respiratory function. In some embodiments a training program or monitoring of a subject may be provided at least in part over the Internet.

In some embodiments, use of an inventive apparatus reduces the severity of at least one symptom of COPD or other respiratory disorder. As noted above, such effect may exist during part of a session and/or may continue for a period of time after a session is over. Such improvement may be assessed using a variety of instruments known in in the art. For example, the Modified Medical Research Council (MMRC) dyspnea scale, baseline dyspnea index (BDI), Borg dyspnea score, and/or the oxygen cost diagram (OCD) may be used. See also GOLD Report and ATC/ERS Guidelines for various approaches to symptom assessment. In some embodiments, use of an inventive breathing assistance apparatus improves the subject's exercise tolerance. For example, a subject may exhibit an improvement in performance on a 6 minute walk test (e.g., an increase in the distance a subject is able to walk in 6 minutes), shuttle walk test, and/or cardiopulmonary exercise testing. See, e.g., ATS Statement: Guidelines for the Six-Minute Walk Test (2002) for discussion of 6 minute walk test. In some embodiments, use of an inventive apparatus provides a clinically meaningful benefit to a subject (e.g., a subject suffering from an obstructive respiratory disorder such as COPD), e.g., within the sound judgement of a health care provider, e.g., a physician, optionally a physician specialized in pulmonary medicine and/or who is experienced in the care of subjects with obstructive respiratory disorders such as COPD. In some embodiments a benefit is evident based on measurement of one or more respiratory parameters or derived parameters. For example, in some embodiments Peak Expiratory Flow rate (PEF), Exhaled Volume (VE), Inhaled Volume (VI), Respiratory Rate (RR), Inhaled and Exhaled Minute Ventilation (MVI and MVE), and/or Inspiratory Capacity (IC) are measured over one or more time periods and compared between unassisted and apparatus-assisted breathing of a subject. In some embodiments, the ratio of MVE and/or VE to MVI and VI respectively are compared between apparatus-assisted and unassisted breathing to evaluate changes in hyperinflation, e.g., over a selected time period following the beginning of a session, such as 1-2 minutes, wherein an increase in MVE or VE to MVI or VI, respectively, indicates a decrease in hyperinflation. In some embodiments, IC is compared between apparatus-assisted and unassisted breathing to evaluate changes in hyperinflation, wherein a greater IC in a subject during apparatus-assisted breathing indicates a decrease in hyperinflation. It should be understood that although COPD is of major interest herein, the inventive apparatus and methods may be used, among other things, for treating other obstructive lung disorders, other conditions in which hyperinflation occurs, and such methods of treatment are aspects of the invention. In some embodiments, the subject suffers from weakness of the respiratory muscles. Such weakness may arise from a variety of causes. For example, individuals who have chronic illnesses and/or who have experienced a period of prolonged physical inactivity (e.g., bedrest) may experience weakness of the respiratory muscles due at least in part, e.g., to muscle wasting. Individuals suffering from congenital or aquired neurological or neuromuscular conditions such as amyotrophic lateral sclerosis (ALS) or myopathic conditions such as myotonic dystrophy may benefit from use of an inventive apparatus.

In some embodiments, a subject has been on mechanical ventilation, e.g., during and/or after a COPD exacerbation, injury, surgery, infection (e.g., pneumonia, sepsis), temporary paralysis (e.g., paralysis from a cause from which a subject would reasonably be expected to be weaned from a ventilator within up to 3-6 months of onset), stroke, and/or due to hypotension, cardiovascular disease (e.g., heart attack, heart failure), shock, altered mental state, respiratory arrest, substance intoxication (e.g., with one or more central nervous system depressants such as alcohol, barbiturate, or opiate), general anesthesia, acute lung injury (e.g., due to trauma, adult respiratory distress syndrome, smoke inhalation, chemical lung injury), epileptic seizure (e.g., status epilepticus), coma, or any other reason. An inventive breathing assistance apparatus may serve as a bridge to help wean the subject from mechanical ventilation. In some embodiments an apparatus is used while the subject remains on mechanical ventilation, e.g., when it is deemed appropriate (e.g., within sound medical judgement) to attempt to wean the patient from the ventilator. In some embodiments a subject has experienced difficulty being weaned from mechanical ventilation, e.g., the subject may have had one or more failed weaning attempts or experienced significant difficulty adjusting to weaning due to ongoing respiratory symptoms. A subject may, for example, have failed one or more spontaneous breathing trials, e.g., one or more spontaneous breathing trials performed using a T-piece while the subject remains intubated or a trial extubation (e.g., the subject may have required re-intubation after being extubated). In some embodiments a subject on mechanical ventilation or recently extubated (e.g., extubated up to 4 weeks previously) may have been on mechanical ventilation, e.g., in an intensive care unit, for at least 1-4 weeks, e.g., 4-24 weeks. In some embodiments an apparatus may be used to provide muscle stimulation while a subject remains intubated, but with the ventilator not providing ventilatory support while the apparatus is in use, or providing only partial ventilatory support while the apparatus is in use. Partial ventilatory support by the ventilator may comprise, e.g., pressure support, delivering at least a minimum number of breaths per minute (e.g., in synchrony with the subject's respiratory effort), or a combination thereof. Use of the apparatus may, for example, help strengthen respiratory muscles (e.g., recovery of muscle strength that may have been lost through disuse) and/or assist a subject in learning or re-learning effective breathing patterns. In some embodiments an apparatus is used during at least some time periods in which the ventilator is providing full ventilatory support, e.g., before weaning is appropriate, in addition to or instead of at such time as weaning is appropriate. Use of the apparatus by a subject who is receiving full ventilatory support may be beneficial e.g., to reduce muscle deconditioning that would otherwise be likely to occur. The apparatus, when operating in this manner, may provide stimulation in synchrony with exhalation based at least in part on signals received from the ventilator and need not sense the subject's breathing, athough it may do so.

In some embodiments an apparatus may be used to assist breathing by a subject who uses or is a candidate for non-invasive ventilatory support, e.g., ventilatory support delivered via a mask. In some embodiments non-invasively delivered ventilatory support comprises continuous positive airway pressure (CPAP). In some embodiments a subject using the apparatus may have a reduced need for or reduced utilization of non-invasive ventilatory support, e.g., as compared with a control subject. As used herein, a subject may be considered to be a "candidate for" a particular therapy if there is, within sound medical judgement, at least a reasonable likelihood that a subject would benefit from a particular therapy, e.g., sufficient likelihood to warrant giving serious consideration to using the therapy or sufficient likelihood to justify a trial of the therapy.

In some embodiments an apparatus may be used to assist breathing by a subject who regularly uses (e.g., at least once a week, e.g., daily) or is a candidate for supplemental oxygen. In some embodiments a subject using the apparatus may have a reduced need for or reduced utilization of supplemental oxygen, e.g., as compared with a control subject.

In some embodiments, the subject does not have partial or complete paralysis of one, more, or all of the expiratory muscles. For example, the subject has not suffered a spinal cord injury (e.g., partial or complete spinal cord transection) or brain injury causing such paralysis. In some embodiments the subject does not have partial or complete paralysis of the diaphragm. In some embodiments, partial paralysis is characterized by reduced function of affected muscles, but there is not a total loss of function. In some embodiments the subject has normal phrenic nerve function. In some embodiments, the subject does not have paraplegia. In some embodiments, the subject does not have tetraplegia. In some embodiments, the subject does not have quadriplegia.

The inventive apparatus may be used by an individual who does not suffer from an obstructive respiratory disorder or who may have an early stage of the disorder which is asymptomatic, undiagnosed, and/or does not warrant therapy. In some embodiments a subject is apparently healthy. In some embodiments a subject has one or more diseases other than an obstructive respiratory disorder. The apparatus may, for example, be used to tone, condition, and/or strengthen abdominal muscle(s). Without wishing to be bound by any theory, at least some persons who wish to tone, condition, and/or strengthen their abdominal muscles may find certain embodiments of the inventive apparatus more comfortable and/or pleasant to use than an abdominal muscle stimulator that delivers a stimulus without regard for whether a subject is inhaling or exhaling. A patient with an obstructive respiratory disorder may benefit from toning, conditioning, and/or strengthening of expiratory muscle(s) that may occur as a result of using an inventive apparatus. Over time the subject's expiratory muscle(s) may become stronger and/or more resistant to fatigue.

In some embodiments an apparatus may be used by a subject who has been or is reasonably expected to be mainly or essentially completely confined to a bed or chair due, e.g., to illness or injury, for an extended period of time, e.g., a period of time sufficient to have a reasonable likelihood within sound medical judgement of resulting in deconditioning (e.g., loss of tone, fitness, and/or strength) of the abdominal muscles. In some embodiments the time is at least 2 weeks, e.g., at least 2-4 weeks. Use of the apparatus may, for example, reduce or prevent muscle deconditioning. In some embodiments the subject is not on mechanical ventilation and has not recently (e.g., within the preceding 4 weeks) been on mechanical ventilation. In some embodiments the subject has been on mechanical ventilation within the preceding 4 weeks. In some embodiments the subject has never been on mechanical ventilation.

The invention encompasses embodiments comprising use of an inventive breathing assistance device together with additional pharmacological or non-pharmacological therapy for an obstructive respiratory disorder. Such additional therapy may include administration of any compound(s) used in the art or potentially useful for treating a subject suffering from an obstructive respiratory disorder, e.g., COPD. In some embodiments, the use of an inventive breathing assistance apparatus allows for a reduction in the use of pharmacological therapy. For example, a patient may be able to avoid using, or reduce their use of, systemic corticosteroids. In some embodiments, a subject may receive training in how to use the apparatus. In some aspects, the training comprises breathing training. In some embodiments, an inventive apparatus is used by a subject participating in a program of pulmonary rehabilitation. In some embodiments, an inventive apparatus is used by a subject engaged in a program of exercise training (which can include endurance (aerobic) and/or strength training). The apparatus may be used during and/or between training sessions.

In some embodiments, a beneficial effect resulting from use of an apparatus described herein by a subject or group of subjects may be demonstrated by comparison with a control subject or control group of subjects. In some embodiments a control subject is an appropriately matched subject who has not used and/or does not use the apparatus. One of ordinary skill in the art would be able to select an appropriate matched control subject. In some embodiments a matched subject is matched with regard to indication for use of the apparatus (e.g., COPD, ventilator weaning, etc.). In some embodiments a matched subject is also matched with regard to severity of the condition, and, optionally, with regard to one or more demographic variables such as age, sex, etc. In some embodiments a historical control subject or group of subjects is used. In some embodiments a subject serves as his or her own control. For example, in some embodiments the subject's condition during use of the apparatus is compared with the subject's condition when not using the apparatus and/or the subject's condition after having used the apparatus regularly for a period of weeks or months is compared with the subject's condition as it existed prior to starting to use the apparatus. In some embodiments a beneficial effect resulting from use of an apparatus described herein may be demonstrated in a clinical trial.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more elements, limitations, clauses, or descriptive terms, found in any other claim that is dependent on the same base claim. Furthermore, where the claims recite a product (e.g., an apparatus or device), it is to be understood that methods of using the product according to any of the methods disclosed herein, and methods of making the product, are included within the scope of the invention, unless otherwise indicated or unless it would be evident to one of ordinary skill in the art that a contradiction or inconsistency would arise. Methods of treating a subject can include a step of providing a subject in need of such treatment (e.g., a subject who has a disease or disorder affecting the respiratory system, such as COPD, and/or who suffers from hyperinflation), a step of diagnosing a subject as having such disease or disorder, a step of selecting a subject for treatment, and/or a step of suggesting an apparatus of the invention to a subject or prescribing an apparatus of the invention for a subject or providing instructions regarding use of the apparatus, e.g., instructions for using the apparatus for one or more purposes.

Where elements are presented as lists, it is to be understood that each subgroup of the elements is also disclosed, and any element(s) can be removed from the group. The invention provides all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. In addition, any particular embodiment, aspect, element, feature, etc., of the present invention may be explicitly excluded from any one or more of the claims.

We claim:

1. A method of treating a subject comprising: (a) sensing an onset of the subject's expiratory phase of breathing with one or more sensors; and (b) delivering a stimulus to the subject's lower anterior thorax or abdomen during at least part of the expiratory phase of breathing in response to said sensing, said stimulus being delivered by mechanical compression using a device comprising an inflatable compartment and effective to cause a contraction in the subject's abdominal muscle so as to assist the subject with ventilation with the proviso that a stimulus is not delivered while the subject is inhaling.

2. The method of claim 1, wherein performing the method decreases the subject's end expiratory lung volume (EELV) as compared with the subject's EELV when unassisted.

3. The method of claim 1, wherein the subject suffers from a disorder that impairs exhalation.

4. The method of claim 1, wherein the subject suffers from chronic obstructive pulmonary disease (COPD).

5. The method of claim 1, wherein the subject has an abnormally high EELV in the absence of the stimulus.

6. The method of claim 1, wherein the subject suffers from dynamic hyperinflation in the absence of the stimulus.

7. The method of claim 1, wherein step (a) comprises detecting respiratory movement of the subject's thorax or abdomen using inductive plethysmography or a strain guage or both.

8. The method of claim 1, wherein the sensor is incorporated into an adhesive patch suitable for placement on the subject's skin.

9. The method of claim 1, wherein the sensing occurs externally to the subject and the stimulus is delivered externally to the subject.

10. The method of claim 1, wherein the sensor, device, or both are incorporated into a garment or belt.

11. The method of claim 1, wherein the sensor and the device are incorporated into the same garment or belt.

12. The method of claim 1, wherein the stimulus is delivered during some but not all respiratory cycles within a session.

13. The method of claim 1, wherein the method comprises analyzing a subject's breathing pattern or activity level and adjusting one or more stimulus parameters based at least in part on the analysis.

14. An apparatus comprising: (a) one or more sensors suitable for detecting when a subject is exhaling; and (b) a device comprising an inflatable compartment adapted to deliver a stimulus to the subject's thorax or abdomen by mechanical compression of the inflatable compartment during at least part of an expiratory phase of the subject's breathing in response to a signal generated by said one or more sensors, said stimulus effective to cause a contraction in the subject's abdominal muscle, with the proviso that the apparatus does not include a device adapted to deliver a stimulus during inhalation.

15. The apparatus of claim 14, wherein the one or more sensors are selected from a strain gauge, a respiratory inductive plethysmography sensor, a piezoelectric sensor, and combinations thereof.

16. The apparatus of claim 14, wherein at least one sensor is incorporated into an adhesive patch suitable for placement on the subject's skin.

17. The apparatus of claim 14, wherein the apparatus is capable of operating in two or more modes, wherein at least one mode comprises delivering, in response to signals generated by said sensor, tactile stimuli that are sufficient to be felt by the subject.

18. The apparatus of claim 17, wherein timing of the tactile stimuli is selected so as to prompt the subject to exhale at least a specified volume or for at least a specified time.

19. The apparatus of claim 18, wherein the apparatus comprises a controller that determines an appropriate stimulus, based at least in part on analyzing the subject's breathing over one or more preceding breathing cycles.

20. A biofeedback method for training a subject to breath more effectively, the method comprising: utilizing the apparatus according to claim 18.

* * * * *

UNITED STATES PATENT AND TRADEMARK OFFICE
CERTIFICATE OF CORRECTION

PATENT NO. : 9,623,239 B2
APPLICATION NO. : 14/858246
DATED : April 18, 2017
INVENTOR(S) : Cedric Francois et al.

Page 1 of 1

It is certified that error appears in the above-identified patent and that said Letters Patent is hereby corrected as shown below:

On the Title Page

Replace the title with the following:
"Apparatus and Methods for Assisting Breathing Using Pneumatic Mechanical Compression"

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*